(12) United States Patent
Shipp et al.

(10) Patent No.: US 7,582,095 B2
(45) Date of Patent: *Sep. 1, 2009

(54) SURGICAL LIGATION CLIP AND METHOD FOR USE THEREOF

(75) Inventors: John I. Shipp, Tullahoma, TN (US); Robert L. Lathrop, Jr., San Jose, CA (US); Robert L. Lathrop, III, San Jose, CA (US); Donald R. Reichel, Saratoga, CA (US); Robert J. Hayes, Gahanna, OH (US)

(73) Assignee: Apollo Camera, L.L.C., Tullahoma, TN (US)

( * ) Notice: Subject to any disclaimer, the term of this patent is extended or adjusted under 35 U.S.C. 154(b) by 627 days.

This patent is subject to a terminal disclaimer.

(21) Appl. No.: 10/619,987

(22) Filed: Jun. 12, 2003

(65) Prior Publication Data

US 2004/0097972 A1    May 20, 2004

Related U.S. Application Data

(63) Continuation of application No. 09/441,898, filed on Nov. 17, 1999, now Pat. No. 6,607,540, which is a continuation of application No. 08/766,193, filed on Dec. 12, 1996, now Pat. No. 5,993,465, which is a continuation of application No. 08/316,730, filed on Oct. 3, 1994, now Pat. No. 5,858,018, which is a continuation-in-part of application No. 08/111,634, filed on Aug. 25, 1993, now abandoned.

(51) Int. Cl.
    *A61B 17/10* (2006.01)
(52) U.S. Cl. ....................... 606/139; 606/142
(58) Field of Classification Search ............. 606/157, 606/158
    See application file for complete search history.

(56) References Cited

U.S. PATENT DOCUMENTS 648,841 A    5/1900    Brosnan (Continued)

FOREIGN PATENT DOCUMENTS

CA    2143560    2/1995

(Continued)

OTHER PUBLICATIONS

Papainoannou, Thanassis, M.S., Daykhovsky, Leon, M.D., Gundfest, Warren S., M.D.: "Safety Evaluation of Laproscopically Applied Clips": *Journal of Laproscopic Surgery* 1996: 6(2): 99-106.

(Continued)

*Primary Examiner*—Anhtuan T Nguyen
*Assistant Examiner*—Tuan V Nguyen
(74) *Attorney, Agent, or Firm*—Martin & Ferraro, LLP

(57) ABSTRACT

The clip applier of the current invention solves the problems of prior art tools by incorporating a pre-clamp mechanism, the function of which is to pre-clamp the vessel to be ligated to a dimension such that the center leg of the spring of the ligation clip need be lifted only slightly. In this manner the spring clip can be slid over the smaller pre-clamped dimension. This insures that the clip spring material will remain within its elastic limit while allowing the tool to maintain a low profile for use in endoscopic surgery, even on large diameter vessels.

19 Claims, 16 Drawing Sheets

U.S. PATENT DOCUMENTS

| | | |
|---|---|---|
| 1,332,287 A | 3/1920 | Genevieve et al. |
| 1,458,797 A | 6/1923 | Beale |
| 1,666,514 A | 4/1928 | Sigler |
| 2,113,991 A | 4/1938 | Larsen |
| 2,498,372 A | 2/1950 | Kortlucke, Jr. et al. |
| 2,626,608 A | 1/1953 | Garland |
| 2,874,384 A | 2/1959 | Krone |
| 2,876,778 A | 3/1959 | Kees, Jr. |
| 3,023,039 A | 2/1962 | Henningsen et al. |
| 3,023,468 A | 3/1962 | Hord et al. |
| 3,032,039 A | 5/1962 | Beaty |
| 3,056,408 A | 10/1962 | Brown |
| 3,098,232 A | 7/1963 | Brown |
| 3,120,230 A | 2/1964 | Skold |
| 3,125,789 A | 3/1964 | Parker |
| 3,270,745 A | 9/1966 | Wood |
| 3,274,658 A | 9/1966 | Pile |
| 3,363,628 A | 1/1968 | Wood |
| 3,439,522 A | 4/1969 | Wood |
| 3,439,523 A | 4/1969 | Wood |
| 3,476,114 A | 11/1969 | Shannon et al. |
| 3,518,993 A | 7/1970 | Blake |
| 3,631,707 A | 1/1972 | Miller |
| 3,675,688 A | 7/1972 | Bryan et al. |
| 3,683,927 A | 8/1972 | Noiles |
| 3,757,629 A | 9/1973 | Schneider |
| 3,777,538 A | 12/1973 | Weatherly et al. |
| 3,827,277 A | 8/1974 | Weston |
| 3,827,438 A | 8/1974 | Kees |
| 3,882,854 A | 5/1975 | Hulka et al. |
| 3,911,923 A | 10/1975 | Yoon |
| 3,955,581 A | 5/1976 | Spasiano |
| 3,989,049 A | 11/1976 | Yoon |
| 4,017,337 A | 4/1977 | Winter et al. |
| 4,024,868 A | 5/1977 | Williams |
| 4,027,510 A | 6/1977 | Hilterbrandt |
| 4,038,987 A | 8/1977 | Komiya |
| 4,041,931 A | 8/1977 | Elliot et al. |
| 4,064,881 A | 12/1977 | Meredith |
| 4,086,926 A | 5/1978 | Green et al. |
| 4,146,130 A | 3/1979 | Samuels et al. |
| 4,152,920 A | 5/1979 | Green |
| 4,169,476 A | 10/1979 | Hilterbrandt |
| 4,170,990 A | 10/1979 | Baumgart et al. |
| 4,196,836 A | 4/1980 | Becht |
| 4,217,902 A | 8/1980 | March |
| 4,226,239 A | 10/1980 | Polk et al. |
| 4,226,242 A | 10/1980 | Jarvik |
| 4,228,895 A | 10/1980 | Larkin |
| 4,241,734 A | 12/1980 | Kandel et al. |
| 4,242,902 A | 1/1981 | Green |
| 4,246,903 A | 1/1981 | Larkin |
| 4,274,415 A | 6/1981 | Kanamoto et al. |
| 4,299,224 A | 11/1981 | Noiles |
| 4,317,451 A | 3/1982 | Cerwin |
| 4,340,061 A | 7/1982 | Kees et al. |
| 4,349,028 A | 9/1982 | Green |
| 4,367,746 A | 1/1983 | Derechinsky |
| 4,372,316 A | 2/1983 | Blake, III et al. |
| 4,374,523 A | 2/1983 | Yoon |
| 4,396,139 A | 8/1983 | Hall et al. |
| 4,412,539 A | 11/1983 | Jarvik |
| 4,418,694 A | 12/1983 | Beroff et al. |
| 4,425,915 A | 1/1984 | Ivanov |
| 4,427,008 A | 1/1984 | Transue |
| 4,430,997 A | 2/1984 | Di Giovanni et al. |
| 4,433,689 A | 2/1984 | von Zeppelin |
| 4,444,187 A | 4/1984 | Perlin |
| 4,448,193 A | 5/1984 | Ivanov |
| 4,449,530 A | 5/1984 | Bendel et al. |
| 4,450,839 A | 5/1984 | Transue |
| 4,450,840 A | 5/1984 | Mericle et al. |
| 4,471,766 A | 9/1984 | Terayama |
| 4,471,780 A | 9/1984 | Menges et al. |
| 4,476,865 A | 10/1984 | Failla et al. |
| 4,478,218 A | 10/1984 | Mericle |
| 4,478,220 A | 10/1984 | Di Giovanni et al. |
| 4,480,641 A | 11/1984 | Failla et al. |
| 4,485,816 A | 12/1984 | Krumme |
| 4,487,205 A | 12/1984 | Di Giovanni et al. |
| 4,492,232 A | 1/1985 | Green |
| 4,493,319 A | 1/1985 | Polk et al. |
| 4,500,024 A | 2/1985 | Di Giovanni et al. |
| 4,509,518 A | 4/1985 | McGarry et al. |
| 4,512,345 A | 4/1985 | Green |
| 4,527,562 A | 7/1985 | Mericle |
| 4,550,715 A | 11/1985 | Santangelo et al. |
| 4,556,058 A | 12/1985 | Green |
| 4,556,060 A | 12/1985 | Perlin |
| 4,557,263 A | 12/1985 | Green |
| 4,562,839 A | 1/1986 | Blake, III et al. |
| 4,569,346 A | 2/1986 | Poirier |
| 4,570,633 A | 2/1986 | Golden |
| 4,590,937 A | 5/1986 | Deniega |
| 4,616,650 A | 10/1986 | Green et al. |
| 4,616,651 A | 10/1986 | Golden |
| 4,620,541 A | 11/1986 | Gertzman et al. |
| 4,624,254 A | 11/1986 | McGarry et al. |
| 4,637,395 A | 1/1987 | Caspar et al. |
| 4,638,804 A | 1/1987 | Jewusiak |
| 4,646,741 A | 3/1987 | Smith |
| 4,658,822 A | 4/1987 | Kees, Jr. |
| 4,660,558 A * | 4/1987 | Kees, Jr. ..................... 606/158 |
| 4,662,373 A | 5/1987 | Montgomery et al. |
| 4,665,906 A | 5/1987 | Jervis |
| 4,671,278 A | 6/1987 | Chin |
| 4,674,504 A | 6/1987 | Klieman et al. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,741,337 A | 5/1988 | Smith |
| 4,765,335 A | 8/1988 | Schmidt et al. |
| 4,777,949 A | 10/1988 | Perlin |
| 4,777,950 A | 10/1988 | Kees, Jr. |
| 4,788,966 A | 12/1988 | Yoon |
| 4,791,707 A | 12/1988 | Tucker |
| 4,796,625 A | 1/1989 | Kees, Jr. |
| 4,796,627 A | 1/1989 | Tucker |
| 4,799,481 A | 1/1989 | Transue et al. |
| 4,821,721 A | 4/1989 | Chin et al. |
| 4,822,348 A | 4/1989 | Casey |
| 4,834,096 A | 5/1989 | Oh et al. |
| 4,844,066 A | 7/1989 | Stein |
| 4,854,317 A | 8/1989 | Braun |
| 4,858,608 A | 8/1989 | McQuilkin |
| 4,869,268 A | 9/1989 | Yoon |
| 4,919,152 A | 4/1990 | Ger |
| 4,934,364 A | 6/1990 | Green |
| 4,943,298 A | 7/1990 | Fujita et al. |
| 4,944,443 A | 7/1990 | Oddsen et al. |
| 4,950,258 A | 8/1990 | Kawai et al. |
| 4,961,743 A | 10/1990 | Kees et al. |
| 4,966,603 A | 10/1990 | Focelle et al. |
| 4,967,949 A | 11/1990 | Sandhaus |
| 4,976,722 A | 12/1990 | Failla |
| 4,979,950 A | 12/1990 | Transue et al. |
| 4,983,176 A | 1/1991 | Cushman et al. |
| 5,002,563 A | 3/1991 | Pyka et al. |
| 5,026,379 A | 6/1991 | Yoon |
| 5,030,226 A | 7/1991 | Green et al. |
| 5,035,692 A | 7/1991 | Lyon et al. |
| 5,037,433 A | 8/1991 | Wilk et al. |
| 5,044,540 A | 9/1991 | Dulebohn |

| | | |
|---|---|---|
| 5,053,045 A | 10/1991 | Schmidt et al. |
| 5,084,057 A | 1/1992 | Green et al. |
| 5,100,420 A | 3/1992 | Green et al. |
| 5,156,608 A | 10/1992 | Troidl et al. |
| 5,156,609 A | 10/1992 | Nakao et al. |
| 5,171,249 A | 12/1992 | Stefanchik et al. |
| 5,171,250 A | 12/1992 | Yoon |
| 5,190,203 A | 3/1993 | Rodak |
| 5,192,288 A | 3/1993 | Thompson et al. |
| 5,197,970 A | 3/1993 | Green et al. |
| 5,207,692 A | 5/1993 | Kraus |
| 5,217,473 A | 6/1993 | Yoon |
| 5,242,456 A | 9/1993 | Nash et al. |
| 5,257,713 A | 11/1993 | Green et al. |
| 5,290,299 A | 3/1994 | Fain et al. |
| 5,300,081 A | 4/1994 | Young et al. |
| 5,340,360 A | 8/1994 | Stefanchik |
| 5,342,373 A | 8/1994 | Stefanchik et al. |
| 5,364,002 A | 11/1994 | Green et al. |
| 5,366,134 A | 11/1994 | Green et al. |
| 5,368,600 A | 11/1994 | Failla et al. |
| 5,383,880 A | 1/1995 | Hooven |
| 5,389,098 A | 2/1995 | Tsuruta et al. |
| 5,395,381 A | 3/1995 | Green et al. |
| 5,431,668 A | 7/1995 | Burbank, III et al. |
| 5,431,669 A | 7/1995 | Thompson et al. |
| 5,439,468 A | 8/1995 | Schulze et al. |
| 5,474,567 A | 12/1995 | Stefanchik et al. |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,527,318 A | 6/1996 | McGarry |
| 5,527,319 A | 6/1996 | Green et al. |
| 5,542,949 A | 8/1996 | Yoon |
| 5,547,474 A | 8/1996 | Kloeckl et al. |
| 5,593,414 A * | 1/1997 | Shipp et al. .................. 606/142 |
| 5,601,573 A * | 2/1997 | Fogelberg et al. ........... 606/143 |
| 5,601,574 A | 2/1997 | Stefanchik et al. |
| 5,620,452 A | 4/1997 | Yoon |
| RE35,525 E | 6/1997 | Stefanchik et al. |
| 5,653,720 A | 8/1997 | Johnson et al. |
| 5,681,330 A | 10/1997 | Hughett et al. |
| 5,695,502 A | 12/1997 | Pier et al. |
| 5,700,270 A | 12/1997 | Peyser et al. |
| 5,700,271 A | 12/1997 | Whitfield et al. |
| 5,702,408 A | 12/1997 | Wales et al. |
| 5,833,700 A | 11/1998 | Fogelberg et al. |
| 5,843,097 A | 12/1998 | Mayenberger et al. |
| 5,849,019 A | 12/1998 | Yoon |
| 5,855,590 A | 1/1999 | Malecki et al. |
| 5,858,018 A | 1/1999 | Shipp et al. |
| 5,897,565 A | 4/1999 | Foster |
| 5,921,997 A | 7/1999 | Fogelberg et al. |
| 5,993,465 A | 11/1999 | Shipp et al. |
| 6,139,555 A | 10/2000 | Hart et al. |
| 6,159,223 A | 12/2000 | Danks et al. |
| 6,193,732 B1 | 2/2001 | Frantzen et al. |
| 6,226,843 B1 | 5/2001 | Crainich |
| 6,290,575 B1 | 9/2001 | Shipp |
| 6,350,269 B1 | 2/2002 | Shipp et al. |
| 6,464,710 B1 | 10/2002 | Foster |
| 6,652,539 B2 | 11/2003 | Shipp et al. |
| 6,652,545 B2 | 11/2003 | Shipp et al. |

FOREIGN PATENT DOCUMENTS

| | | |
|---|---|---|
| DE | 2330182 | 1/1975 |
| DE | 3722311 | 1/1989 |
| DE | 3802651 | 8/1989 |
| DE | 40 15 562 | 11/1991 |
| GB | 2071751 | 9/1981 |
| JP | 6237939 | 8/1994 |
| SU | 1389 762 | 4/1988 |
| SU | 1389792 | 4/1988 |
| WO | WO 87/06118 | 10/1987 |
| WO | WO 90/02522 | 3/1990 |
| WO | WO 90/03763 | 4/1990 |
| WO | WO 95/05778 | 3/1995 |

OTHER PUBLICATIONS

Nelson, Timothy M., M.D., Nakashima, Masanobu, M.D., Mulvihill, Sean J., M.D.: "How Secure Are Laproscopically Placed Clips? An In Vitro and In Vivo Study": *Arch Surg.* 1992: 127:718-720: pub. Dec. 8, 1991.

Arnaud, Jean-Pierre, M.D., Bergamaschi, Roberto, M.D.,: "Migration and Slipping of Metal Clips After Celloscopic Cholecystectomy": *Surgical Laproscopy & Endoscopy* 1993: 3(6): 487-488: pub. 1993 Raven Press, Ltd., New York.

Klein, R.D., Jessup, G., Ahari, F., Connolly, R.J., Schwaitzberg, S.D.: "Comparison of titanium and absorbable polymeric surgical clips for use in laproscopic cholecystectomy": *Surgical Endoscopy* 1994: pub. 1994 Springer-Verlag New York Inc..

* cited by examiner

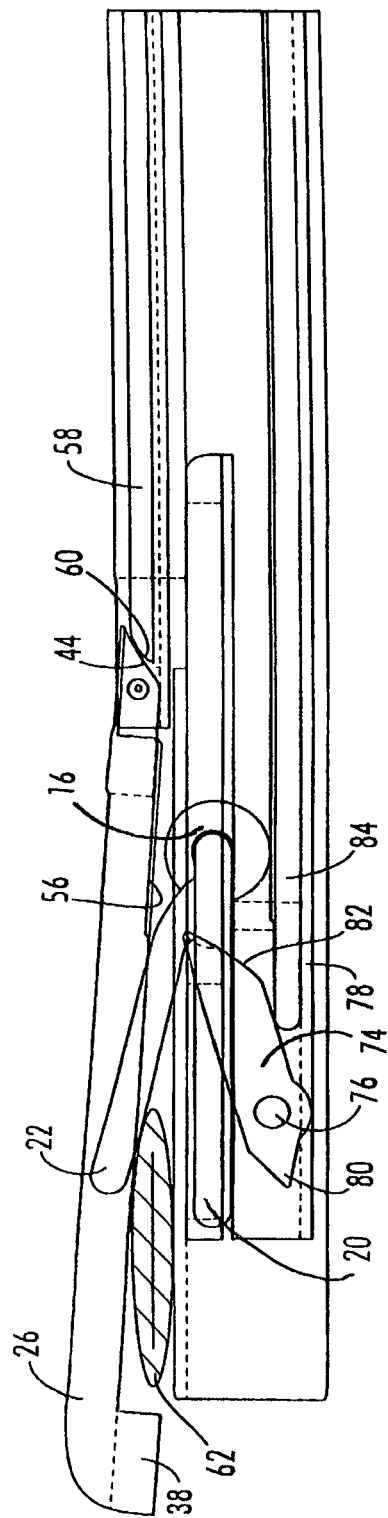
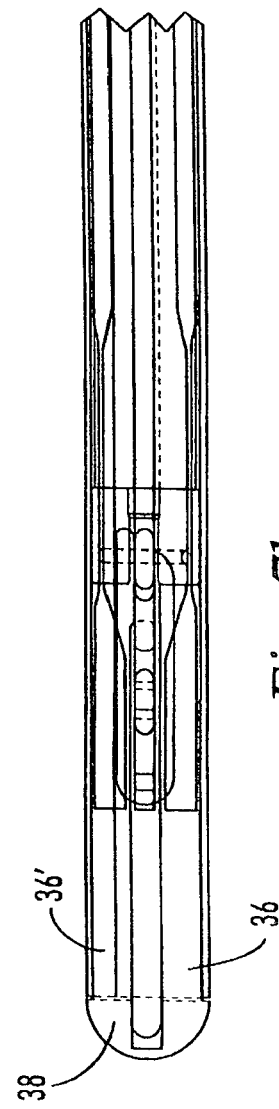
Fig. 7a
Fig. 7b

SURGICAL LIGATION CLIP AND METHOD FOR USE THEREOF

The present application is a continuation of application Ser. No. 09/441,898, filed Nov. 17, 1999 now U.S. Pat. No. 6,607,540; which is a continuation of application Ser. No. 08/766,193, filed Dec. 12, 1996, now U.S. Pat. No. 5,993,465; which is a continuation of application Ser. No. 08/316,730, filed Oct. 3, 1994, now U.S. Pat. No. 5,858,018; which is a continuation-in-part of application Ser. No. 08/111,634, filed Aug. 25, 1993, now abandoned; the disclosure of which is incorporated by reference herein.

BACKGROUND OF THE INVENTION

1. Field of the Invention

The present invention relates generally to mechanical devices used in surgical procedures to obtain ligation or hemostasis, and more particularly, to low profile tools that can apply a preformed, spring loaded ligation clip used during surgery to clamp around a vessel or duct, such as the cystic duct, and thereby obtain ligation.

2. Description of the Prior Art

It will be appreciated by those skilled in the art that the use of ligation clips to control bleeding during surgical procedures is well known. As described, for example, in U.S. Pat. Nos. 4,976,722 and 4,979,950, prior art clips are generally formed of metal wire, usually a titanium alloy, having a "U-shaped" rectangular cross-section. Such prior art clips often include a grooved pattern machined into the inner or clamping surfaces of the clip, in an attempt to enhance the ability of the clip to remain in position after it is closed around the vessel. Application of the clip to the vessel is normally effected by means of a crushing action produced by a clip applier, such as that disclosed in U.S. Pat. No. 5,030,226. Such crushing actions, of course, permanently deform the clips, making them difficult to remove or re-position.

Prior art surgical ligation clips have several inherent problems. For example, the force applied by the clip to the vessel can be variable and inconsistent from one clip to the next, because of the variation in crushing force applied to the clip by the user. Further, prior art clips have a tendency to slip off the end of the blood vessel stub (i.e., parallel to the axis of the vessel) to which it has been applied, because of the low coefficient of friction associated with the clip, and lack of adequate restraining force provided by the clip. Because of this, separation of the clip from the vessel to which it has been applied, after the wound has been closed, is not uncommon. A related problem found in the prior art is the fact that the ligating or restraining force offered by the crushed clip varies along the length of the clip, decreasing toward the open end. Thus, the section of the vessel near the open end of the clip can be inadequately ligated.

It is also common in the prior art to actually form and crush the clip only at the time of its application to the targeted blood vessel. It is often required that vessels of 4 mm and larger diameter be ligated. Because most clips of the prior art have no spring action it is required that the inside clearance dimension of the clip, prior to crushing, be larger than the vessel. This does not lend itself to clip applier designs that will pass through small 5 mm trocars. Accordingly, the clip applier mechanism of the prior art must be relatively large and cumbersome. This is a particular problem in laparoscopic procedures, during which both the clip and clip applier must be inserted through a trocar placed through the patient's external tissues and into the surgical field. Thus, prior art ligation clip appliers used in laparoscopic procedures universally consist of a 10 mm diameter clip applier that can fit only through a trocar having a 10 to 11 mm diameter entry port. Because one goal of laparoscopic surgery is to minimize the size of the entry wound, a surgical ligation clip and clip applier that can be used within a 5 mm diameter trocar port is highly desirable.

To address these problems, a new and improved surgical clip was designed, as illustrated in FIGS. 1 and 2 and in U.S. patent application Ser. No. 08/111,634 filed on Aug. 25, 1993. The improved clip has a vessel clamping arm, a vessel support member, and at least one tension coil integrally joining the arm and support member. The clip is pre-formed so that in its equilibrium state, it can be easily placed within the surgical field, including through an endoscopic trocar port with as little as a five millimeter diameter. After the clip is placed proximate the blood vessel or duct to be clamped, the clamping arm is moved from its equilibrium position to a position under higher tension, allowing positioning of the vessel between the arm and support member. When correct placement and positioning is achieved, the arm is released and, as the arm tends to move back towards its equilibrium position, it clamps the vessel between the arm's curved lower surface and the supporting upper surface of the vessel support member.

To enhance the performance of the tension coil(s), the vessel support member includes first and second arms, one of which terminates in a loop section. Minimal cross-sectional area of the clip is achieved by substantially longitudinally aligning the vessel support member, the clamping arm, the loop section, and the tension coil.

The clamping arm is pre-formed into an equilibrium that generally aligns with the horizontal plan of the support member. A second embodiment of the clip pre-loads the clamping arm into a relaxed position where the free end of the arm rests against the upper surface of the support member.

Unfortunately, several problems are encountered in applying this novel pre-formed, spring-action ligating clip onto a vessel through a 5 mm trocar port. First, the nominal 5 mm cross section of the clip that is inserted through the trocar places severe design restrictions on any applier mechanism. Traditional "crush type" clips require a crusher and anvil type applier mechanism which is too large to pass through a 5 mm trocar. Second, care must be taken so that the elastic limit of the spring material is not exceeded when the clip is opened up so that it can be placed over the vessel diameter. For titanium wire of diameter 0.75 mm, for example, lifting the distal end of the center leg of the spring much above 2 mm will exceed the elastic limit.

What is needed, then, is a clip applier tool that may be used to place a pre-formed, spring action ligation clip around a large diameter vessel without permanently deforming or weakening the clip, one that will compress, without crushing, the vessel, and yet be small enough to use through a 5 mm trocar.

SUMMARY OF THE INVENTION

The clip applier of the current invention solves the problems of prior art tools by incorporating a pre-clamp mechanism, the function of which is to pre-clamp the vessel to be ligated to a dimension such that the center leg of the spring of the ligation clip need be lifted only slightly. In this manner the spring clip can be slid over the smaller pre-clamped dimension. This insures that the clip spring material will remain within its elastic limit while allowing the tool to maintain a low profile for use in endoscopic surgery, even on large diameter vessels.

These and other objects of the present invention will be apparent from review of the following specification and the accompanying drawings.

BRIEF DESCRIPTION OF THE DRAWINGS

FIGS. 7a and 7b show side and top views respectively of the device with the pre-clamp arm pressing a vein and the clip opened for engagement with the vein.

DETAILED DESCRIPTION OF THE PREFERRED EMBODIMENT

Figure 1:
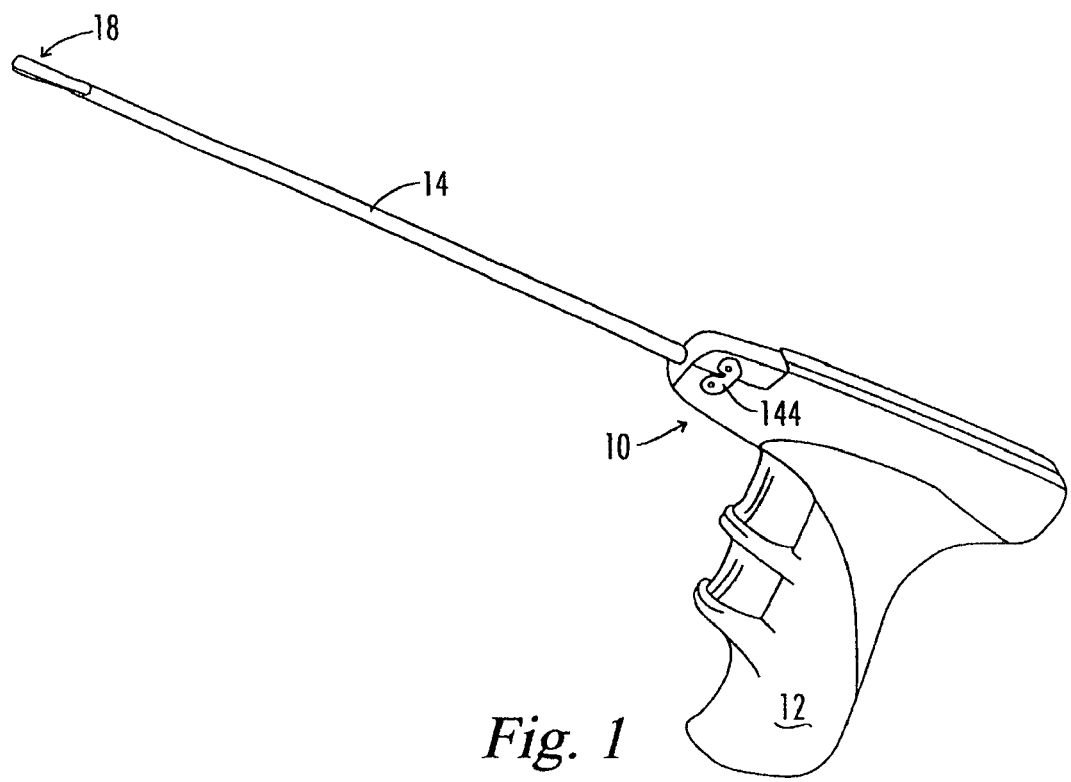
FIG. 1 is a perspective view in a somewhat schematic form of the device of the present invention.

Referring now to FIG. 1, there is shown generally the preferred embodiment of the present clip applier. The device is indicated generally by the numeral 10. The device 10 includes the pistol grip 12 and an applicator sleeve 14. The applicator sleeve 14 contains a number of ligation clips 16 all in stacked relation and held in position in the manner hereinafter described. The ligation clips 16 are stacked generally in the trunk portion of the applicator sleeve 14 and extend from the end of the sleeve 14 that is connected to the pistol grip 12 toward the distal end 18 of the device 10.

Figure 2A:
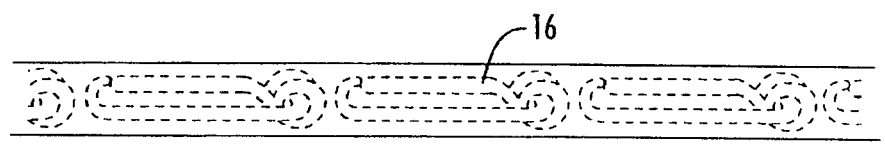
FIG. 2a illustrates in perspective the clips of the present invention within the cartridge of the device.
Figure 2B:
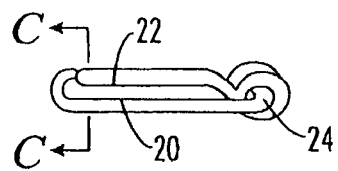
FIG. 2b illustrates a perspective view of one embodiment of a ligation clip according to the present invention having a base (or support member) and a pressure arm (or clamping arm) for which the applicator of the present invention is designed.

FIG. 2b shows the shape and construction of a typical ligation (or surgical) clip 16 which device 10 of the present invention is designed to apply during surgical procedures. Ligation clip 16, additional preferred embodiments of which are shown in FIGS. 2e-2h and FIGS. 2i and 2j, is formed generally of a resilient, continuous, wire type material such as titanium or stainless steel, preferably round in cross section. Ligation clip 16 is bent to define a base (or support member) 20 and a pressure arm (or clamping arm) 22. Base 20 and pressure arm 22 are connected at their proximate end 24.

Figure 2C:
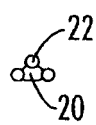
FIG. 2c is a cross section of the ligation clip of FIG. 2b along the line C-C of FIG. 2b.
Figure 2D:
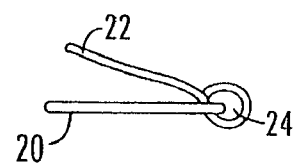
FIG. 2d is a side view of the ligation clip shown in FIG. 2b with the ligation clip opened.
Figure 2E:
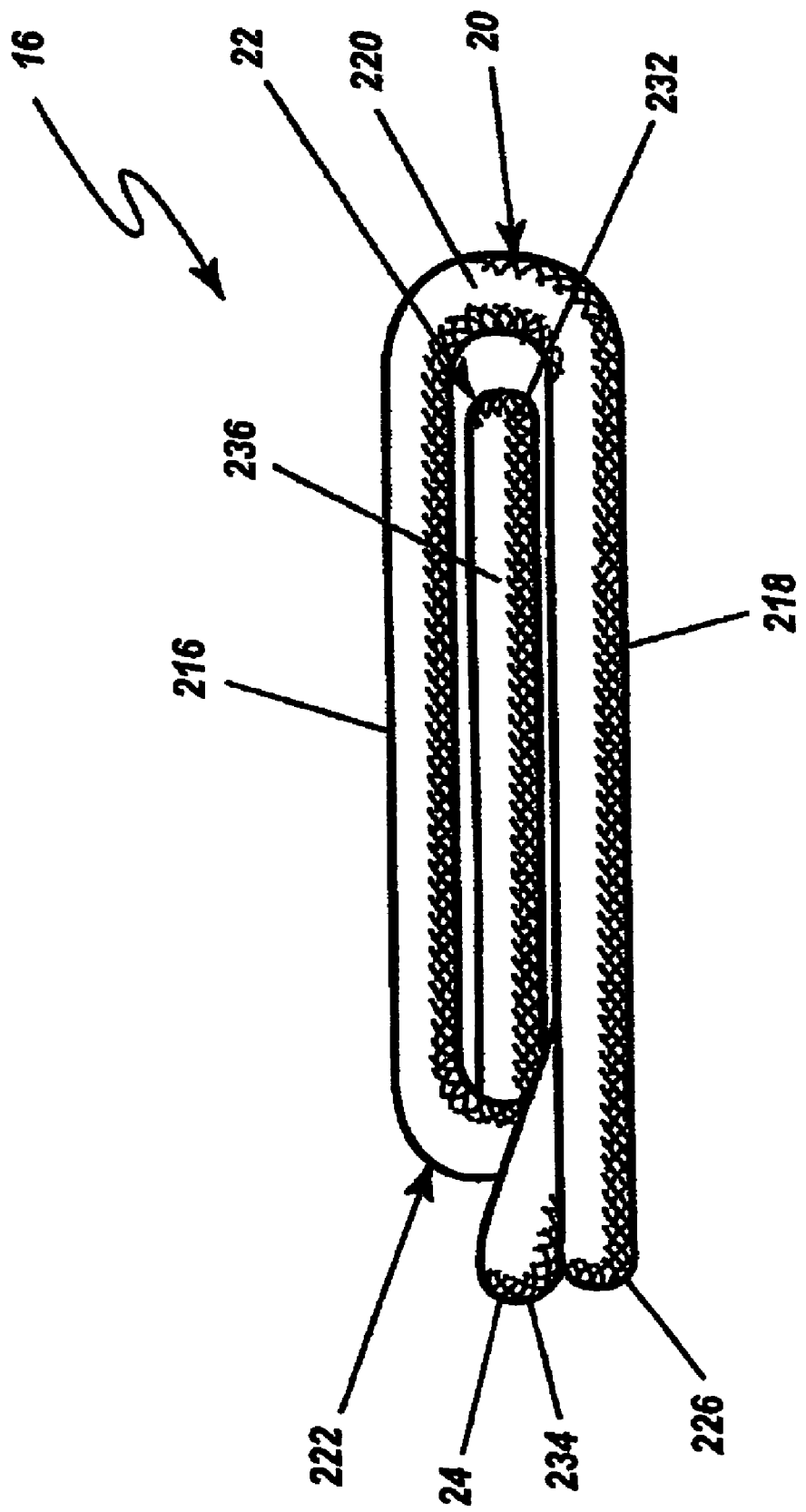
FIG. 2e is a top view of another embodiment of a ligation clip according to the present invention having a base (or support member) and a pressure arm (or clamping arm).
Figure 2F:
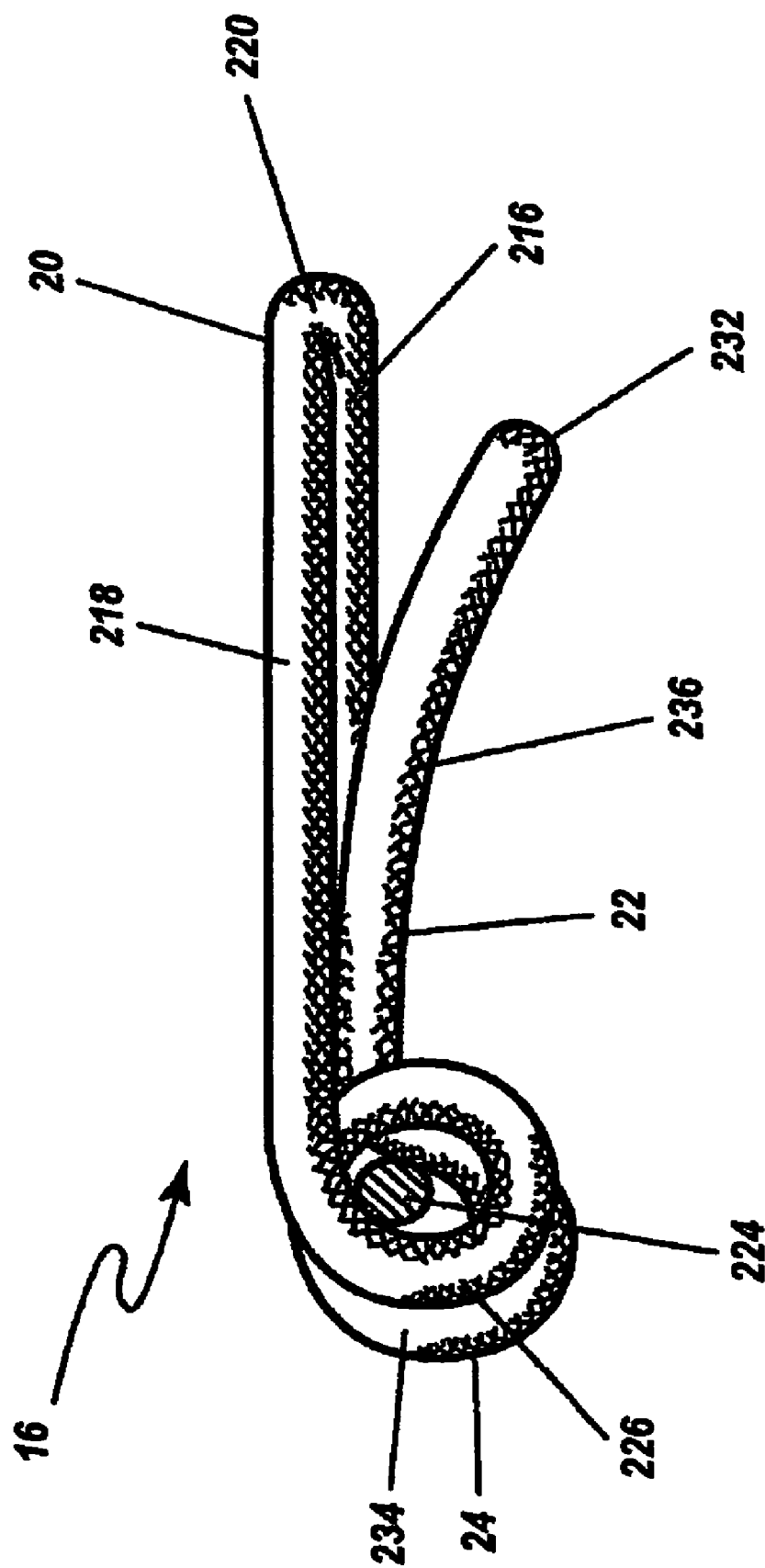
FIG. 2f is a side view of the ligation clip of FIG. 2e.
Figure 2G:
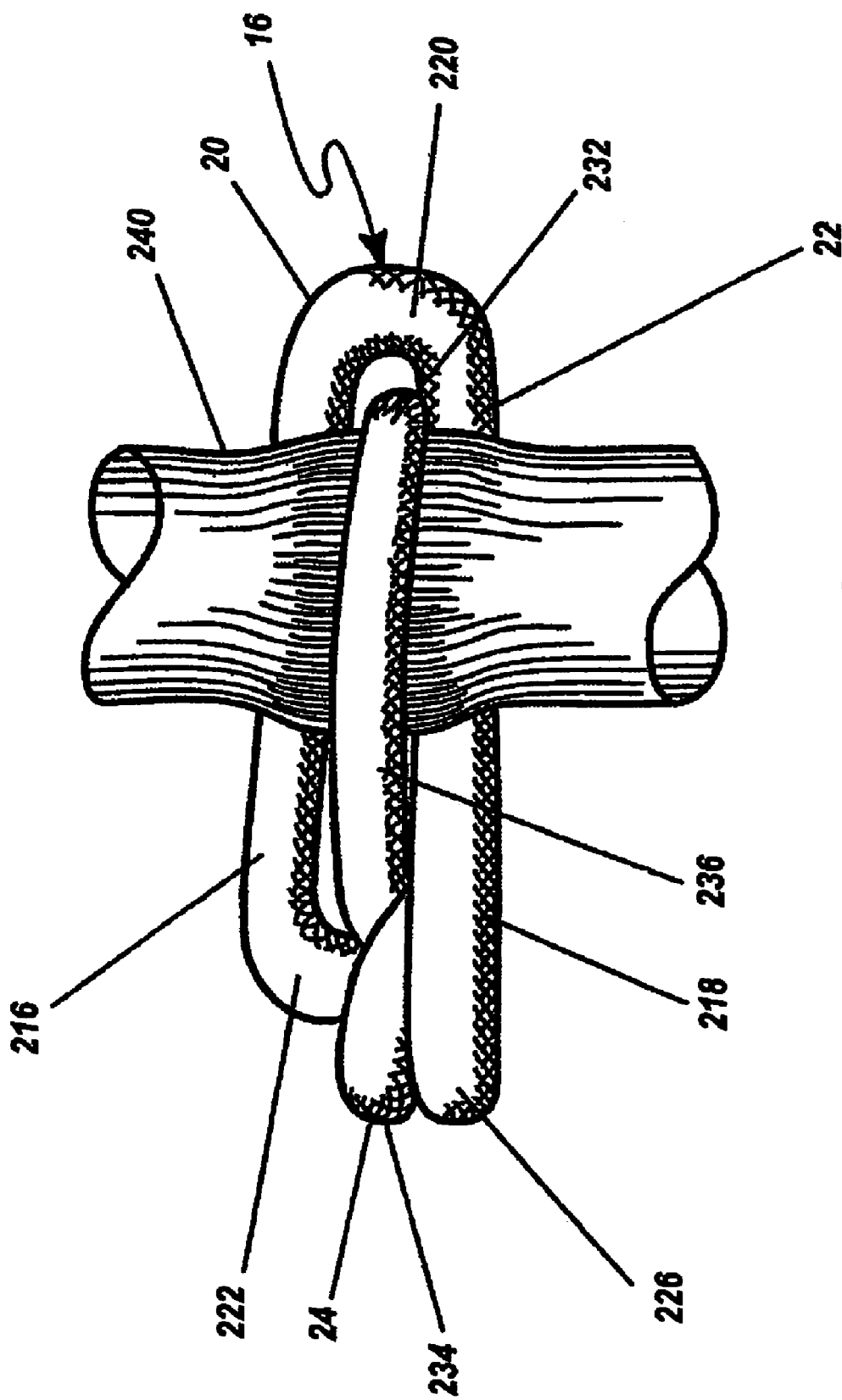
FIG. 2g is a top view of the ligation clip of FIGS. 2e and 2f after application to a blood vessel with the pressure arm in a clamped position.
Figure 2H:
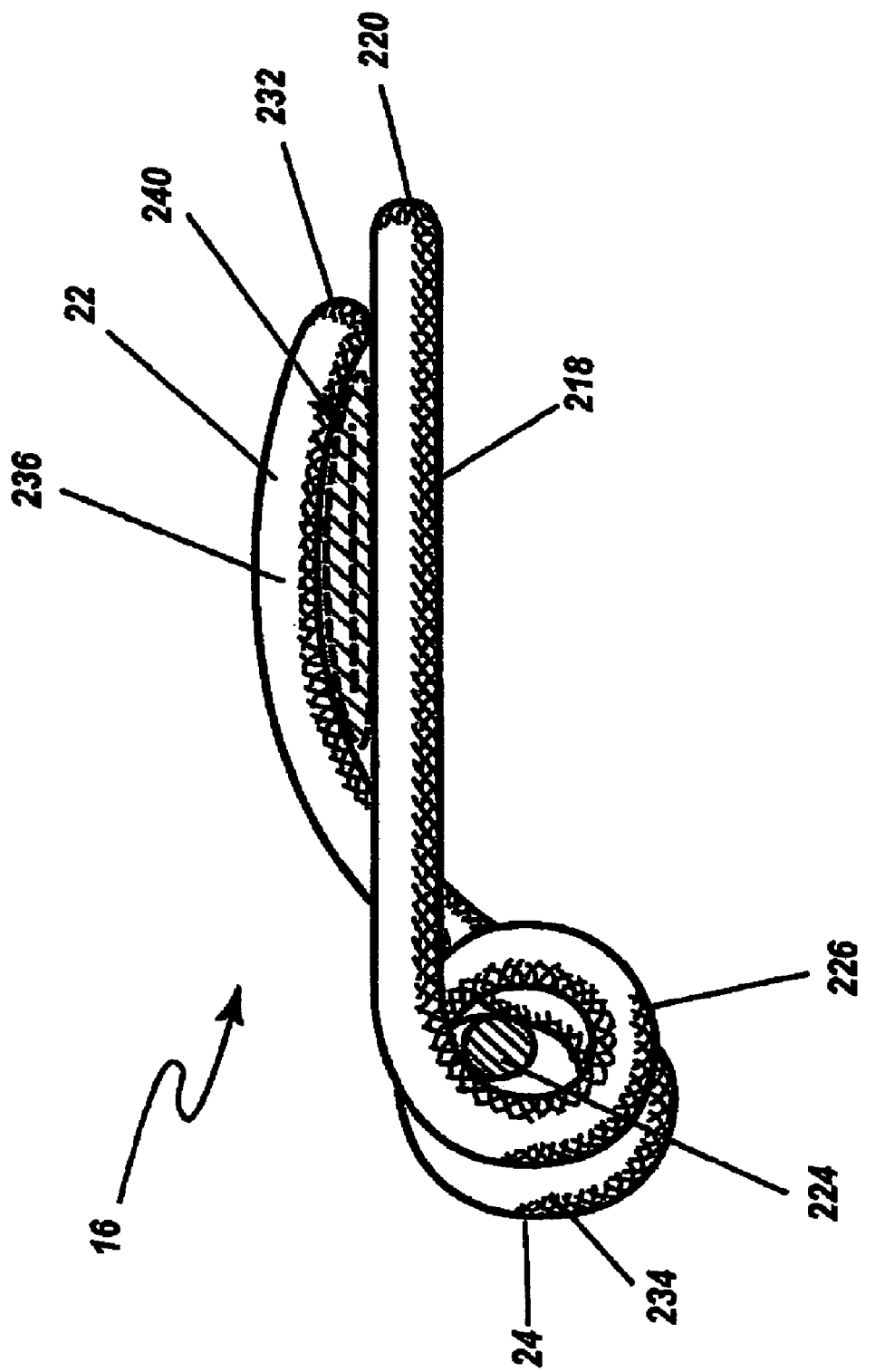
FIG. 2h is a side view of the ligation clip of FIGS. 2e and 2f after application to a blood vessel with the pressure arm in a clamped position.
Figure 2I:
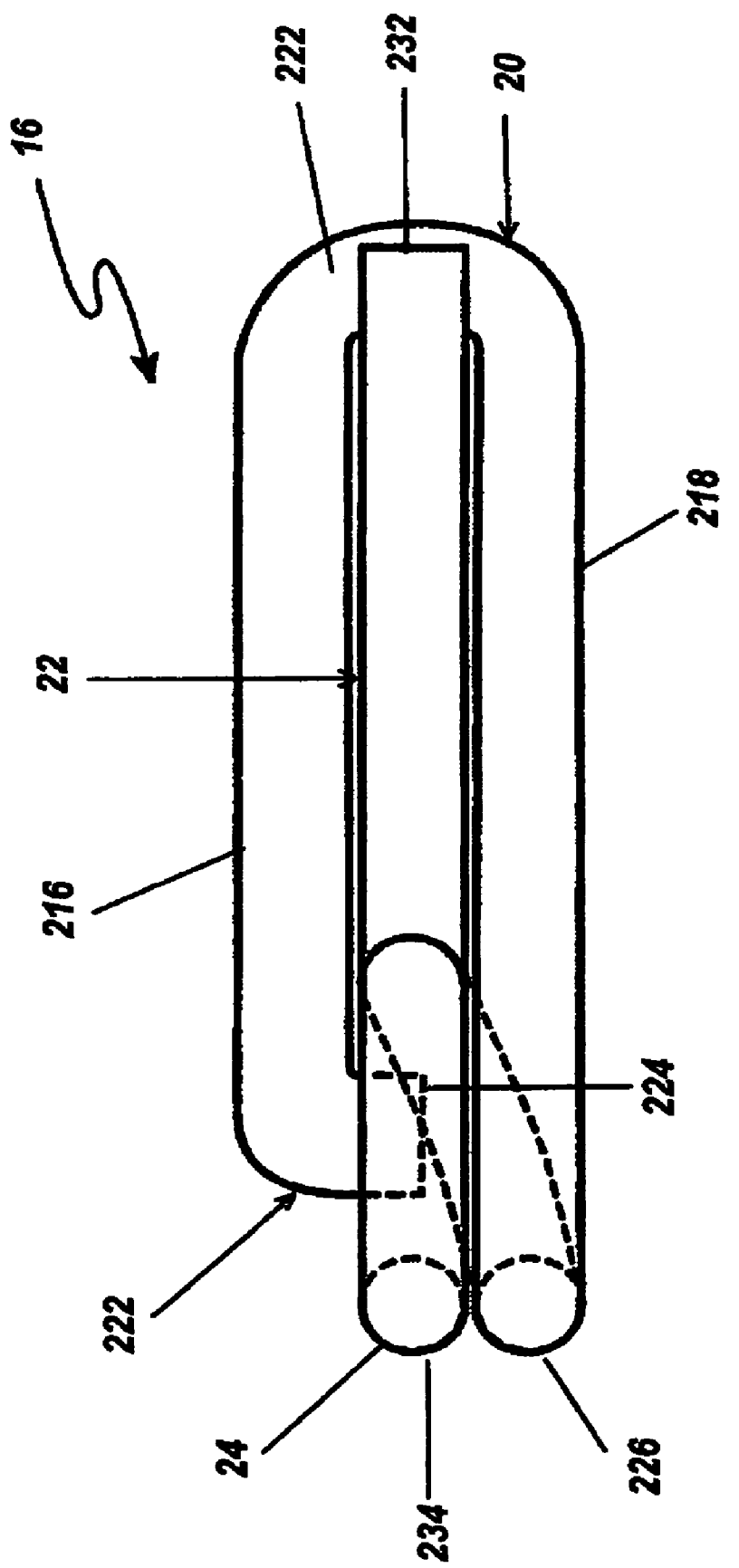
FIG. 2i is a top view of another embodiment of a ligation clip according to the present invention having a base (or support member) and a pressure arm (or clamping arm).

As shown, for example, in FIGS. 2e and 2i, base (or support member) 20 of ligation clip 16 is an elongated U-shaped structure including a first leg 216 and a second leg 218 joined by a one hundred eighty degree (180°) bend section 220. First leg 216, second leg 218, and bend section 220 form a channel therebetween.

As shown in FIGS. 2b and 2f, for example, in preferred embodiments, base 20 can be straight. In another preferred embodiment, first leg 216 and second leg 218 of base 20, for example, as shown in FIG. 2i, can be curved upwardly to enhance the clamping force distribution characteristics of ligation clip 16. It will be apparent to those skilled in the art that, as in ligation clip 16 of FIGS. 2e-2h, such curvature could be provided alternatively or additionally within pressure arm 22. Where ease of manufacture is a prime objective, each of first leg 216, second leg 218, and base 22 can be straight.

In a preferred embodiment, a proximal free end 224 of ligation clip 16 is joined by a ninety degree (90°) bend section 222 to first leg 216. As shown in FIG. 2f, for example, proximal free end 224 and a segment of bend section 222 is centrally disposed within tension coil 234. As shown in FIGS. 2e and 2i, first leg 216 terminates at its proximal end (away from bend section 220) at bend section 222. Furthermore, as shown in FIGS. 2e and 2i, second leg 218 terminates at its proximal end (away from bend section 220) in a loop section 226. Loop section 226 loops inwardly toward pressure arm 22, as shown, for example in FIGS. 2e and 2i, and resides in a vertical plane perpendicular to the horizontal plane of base 20.

Figure 2J:
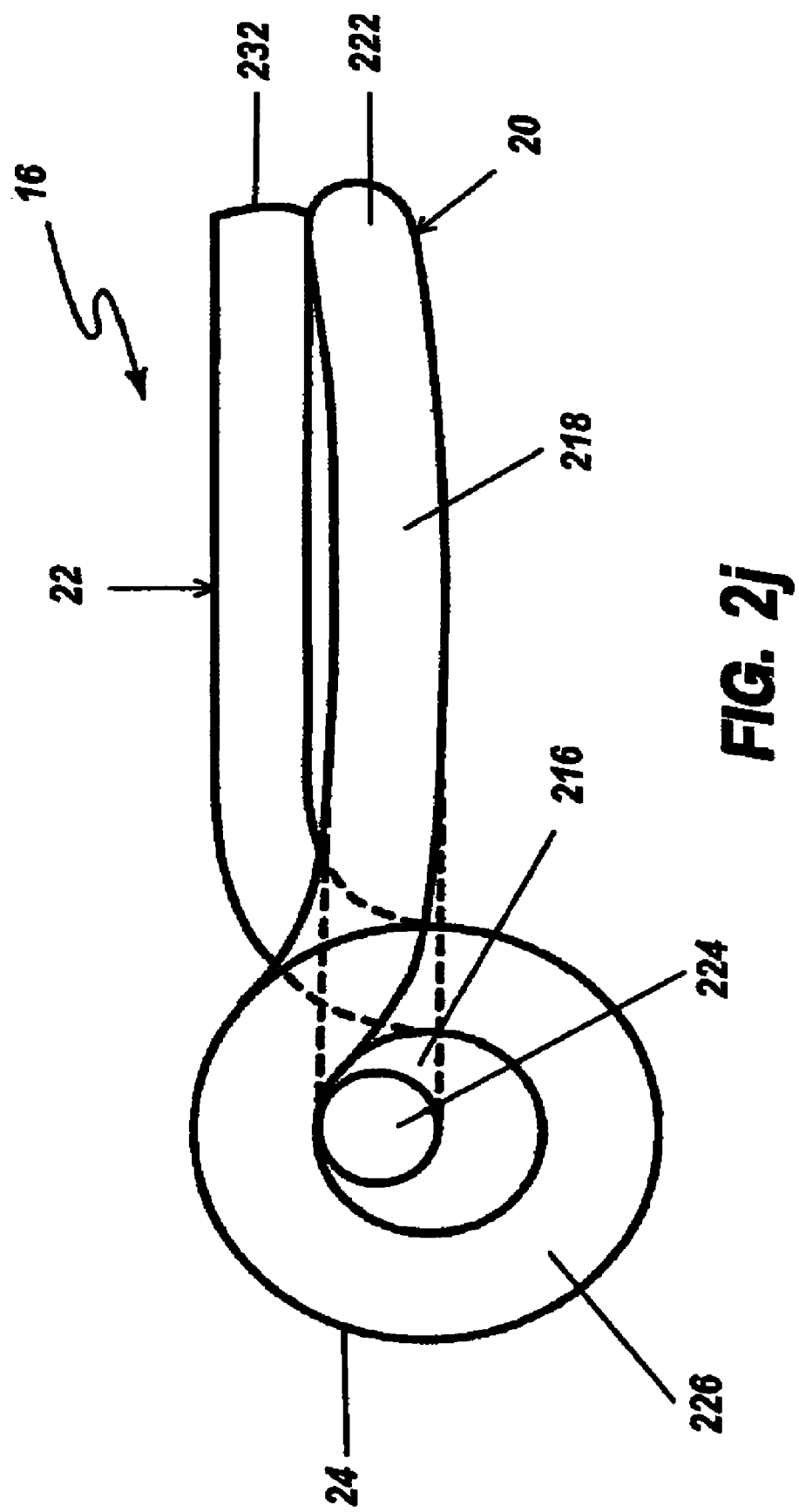
FIG. 2j is a side view of the ligation clip of FIG. 2i.

Pressure arm 22 terminates at a tension coil 234, and a distal free end 232 thereof defines the beginning of pressure arm 22. As shown in FIGS. 2b and 2c, pressure arm (or clamping arm) 22 can overlie and extend generally parallel to base 20 and be positioned directly above the channel of base 20. In another preferred embodiment, pressure arm 22, as shown in FIGS. 2f and 2h, can include a curved section 236. Curved section 236 of pressure arm 22 moves proximately away from distal free end 232, terminating in tension coil 234. In yet another preferred embodiment, pressure arm 22, as shown in FIG. 2j, can overlie and extend generally parallel to base 20, be positioned directly above the channel of base 20, and contact bend section 220.

The vertical plane established by tension coil 234 is oriented in substantial alignment with the vertical plane of loop section 226, and, accordingly, perpendicular to the horizontal plane of base 20. Loop section 226 and tension coil 234 form the connection between base 20 and pressure arm 22. It will be apparent to those skilled in the art that the orientation of loop section 226 and tension coil 234, and by forming ligation clip 16 of a continuous piece of resilient material, movement of pressure arm 22 will place, as discussed below, pressure arm 22 under tension with respect to base 20. Furthermore, such an orientation will minimize the width and cross-sectional area of ligation clip 16 which is preferred, particularly in laparoscopic surgery.

When ligation clip 16 of FIGS. 2a-2d is in an at rest position, pressure arm 22 overlies and extends generally parallel to base 20 and is positioned directly above the channel of base 20. When ligation clip 16 of FIGS. 2e-2h is in an at rest position, pressure arm 22 is longitudinally aligned with and oriented between first leg 216 and second leg 218 of base 20, but, as shown in FIG. 2f, below the horizontal plane defined by first leg 216 and second leg 218. When ligation clip 16 of FIGS. 2i and 2j is in an at rest position, pressure arm 22 rests in a preloaded condition on the upper surface of base 20 at bend section 220.

To open ligation clip 16, pressure arm 22 can be rotated about the point of connection between base 20 and pressure arm 22 at proximate end 24 to open ligation clip 16. That is, when ligation clip 16 is opened, pressure arm 22 is pivoted about the connection point between base 20 and pressure arm 22. The connection between base 20 and pressure arm 22 at proximate end 24 is a spring type connection (i.e., loop section 226 and tension coil 234) that tends to bias pressure arm 22 back into the at rest position as described previously.

Ligation clip 16 may be opened by separating pressure arm 22 from base 20. That separation occurs when base 20 is held in position and pressure arm 22 is forced away from base 20 (as shown, for example, in FIG. 2d). As shown in FIG. 2d, pressure is applied to pressure arm 22 to force it to rotate clockwise about the pivotal connection at proximate end 24 between base 20 and pressure arm 22. However, when the pressure is released from pressure arm 22, pressure arm 22 will rotate about the connection point between base 20 and pressure arm 22 at proximate end 24 in a counter clockwise position back into the at rest direction (as shown in FIGS. 2a and 2b).

Looking now at FIGS. 2g and 2h, application of ligation clip 16 of FIGS. 2e-2h to a blood vessel 240 to achieve hemostasis is shown. After ligation clip 16 is placed in the surgical field adjacent to the targeted blood vessel 240, pressure arm 22 is moved upwardly between first leg 216 and second leg 218 to define a gap and space between distal free end 232 and the upper surface of bend section 220. For most uses, a vertical gap of approximately 1.5 mm will be sufficient between distal free end 232 and bend second 220. Ligation clip 16 is then maintained in this position so that blood vessel 240 can be manipulated within the space created between base 20 and pressure arm 22. Pressure arm 22 is then released, trapping vessel 240 within ligation clip 16 as pressure arm 22 moves toward its relaxed position.

The curvature of curved section 236 of pressure arm 22 causes a relatively consistent clamping pressure to be placed over the entire surface of blood vessel 240, thereby achieving effective hemostasis. By placing loop section 226 physically adjacent to, and operatively in series with tension coil 234, a smoother, more consistent application of hemostatic force is obtainable, while increasing the resistance of ligation clip 16 to deformation.

It will be apparent to those skilled in the art that ligation clip 16 is also effective in clamping off ducts connecting various organs, the cystic duct, for example. Accordingly, where the term "vessel" is used herein, it is intended that such reference include all fluid carrying body structures within the surgical field where ligation or clamping is needed.

Where the diameter of the duct or other structure to be clamped is substantially larger than 1.5 mm, a slightly modified method of applying ligation clip 16 is preferred so that the elastic limit of the material used in the construction of ligation clip 16 is not exceeded. In such modified technique, surgical pliers (not shown) of conventional design are first positioned over the area to be clamped and the duct or other structure is then compressed to approximately a two wall thickness, or 1.5 mm. The pliers are then removed and ligation clip 16 applied as described above. To minimize the risk of overcompression, the pliers will preferably include a means for limiting closure of its laws to a minimum spacing of approximately 1.5 mm. The use of this technique on large structures allows ligation clip 16 to be formed with a minimized profile suitable for use in a 5 mm trocar, even if the diameter of the duct or other structure to be clamped, for example, exceeds 5 mm.

To remove or re-position ligation clip 16, pressure arm 22 needs merely to be moved back up into its fully unclamped position, blood vessel 240 and ligation clip 16 manipulated as needed, and then pressure arm 22 is released towards its relaxed position.

Adding a series of ridges, notches, burrs by machining, etching, or other treatment to the clamping surfaces of base 20 and pressure arm 22 can enhance the gripping force of clip 16.

To achieve the objective of minimizing the cross-sectional area of ligation clip 16 of FIGS. 2e-2h, thereby permitting it to be used in laparoscopic surgical procedures, ligation clip 16 is pre-formed into the position substantially as shown on FIGS. 2e and 2f. As such, first leg 216, second leg 218, pressure arm 22, tension coil 234, and loop section 226 are substantially in alignment longitudinally. Furthermore, by extending and preloading pressure arm 22 of ligation clip 16 of FIGS. 2i-2j so that it can assume the position shown in FIG. 2j, the cross-sectional area presented by ligation clip 16 is further minimized, rendering it more adaptable for use in small diameter trocars. Preloading pressure arm 22, of course, helps to maintain ligation clip 16 of FIGS. 2i and 2j in a narrow profile until it is positioned for application.

As shown in FIGS. 2e-2h, in a referred embodiment of ligation clip 16 adaptable for placement within an endoscopic surgical field through a 5 mm diameter trocar port, the inside diameters of loop section 226 and tension coil 234 are approximately 3 mm. The length of ligation clip 16, measured from the proximal surface of tension coil 234 to the distal surface of bend section 220 is approximately 12 mm. The width of base 20, measured at the outside surfaces of first leg 216 and second leg 218, is approximately 2.5 mm. Pressure arm 22 is approximately 9 mm from distal free end 232 to its intersection with tension coil 234. In the preferred embodiment of ligation clip 16 of FIGS. 2e-2h, curved section 236 of pressure arm 22 will have a radius of curvature of approximately 25 mm.

A suitable material from which ligation clip 16 can be formed is wrought titanium 6A1-4V ELI alloy wire having a nominal diameter of 0.75 mm, and which meets ASTM Standard F136-92. Ligation clip 16 can also be made of wire having a non-circular cross section, or formed from wire having a combination of circular and non-circular sections. For example, tension coil 234 and/or pressure arm 22 could be stronger if formed from rectangular-shaped wire.

When the ligation clip is applied to a blood vessel or artery, the pressure arm 22 is "opened" from the base 20. The clip is inserted over the blood vessel so that the blood vessel traverses generally perpendicularly to the direction of the legs of the U-shaped base 20 over the top of the base 20 and beneath the pressure arm 22. When the force that causes the pressure arm 22 to open from the base 20 is released, the pressure arm 22 captures the blood vessel between the underside of the pressure arm 22 and the top of the base 20 to compress the blood vessel and close it.

Figure 3:
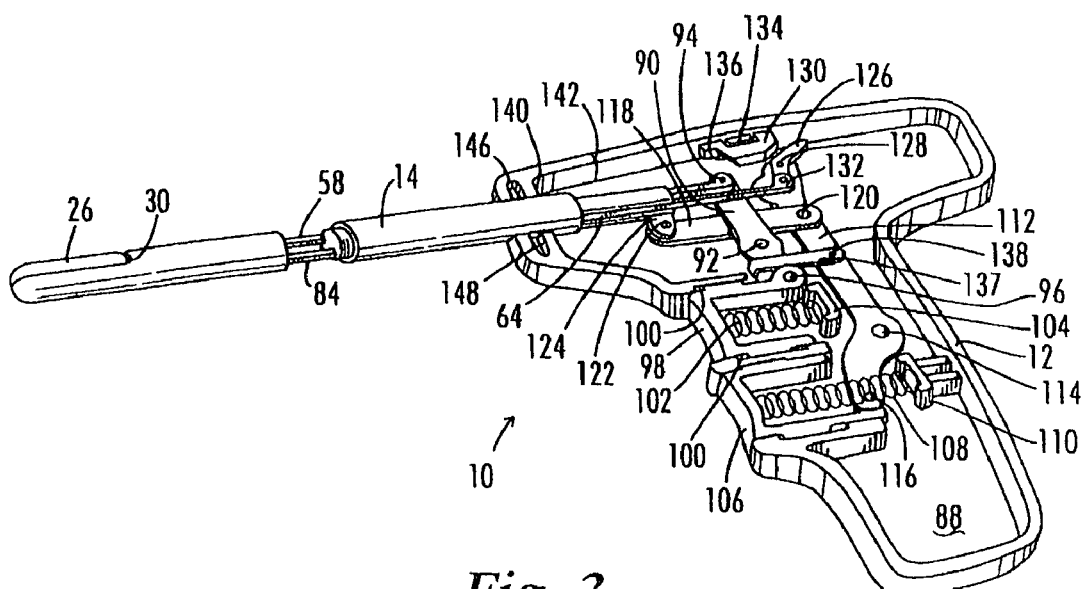
FIG. 3 shows a perspective view of the device of the present invention.

Referring now to FIG. 3, at the distal end 18 of the device 10, there is shown generally a pre-clamp arm 26. Pre-clamp arm 26 can also be seen in FIGS. 6*a* and 7*a*. FIGS. 4*a*-10*c* all show various views and positions of the mechanism at the distal end 18 of the device 10.

Figure 4C:
FIGS. 4a, 4b and 4c show side, top and end views of the device of the present invention in the at rest position.
Figure 4B:
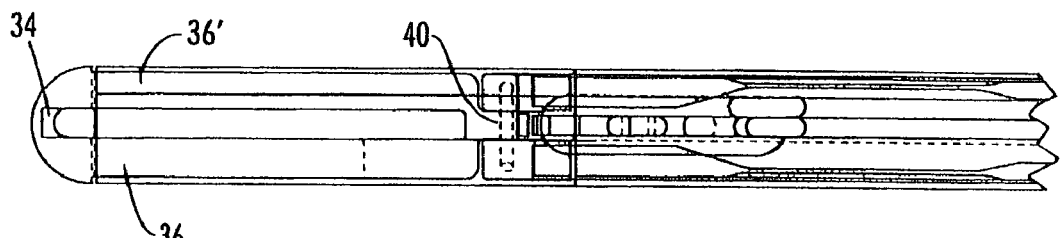
Figure 4A:
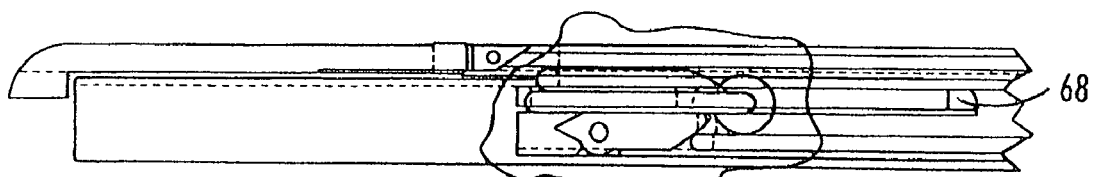
Figure 5A:
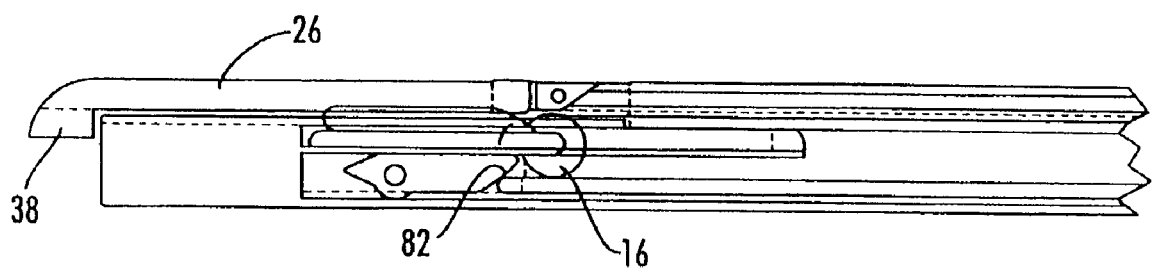
FIGS. 5a, 5b and 5c show side, top and end views respectively of the device of the present invention with the clip assembly advanced to the ready position.
Figure 5B:
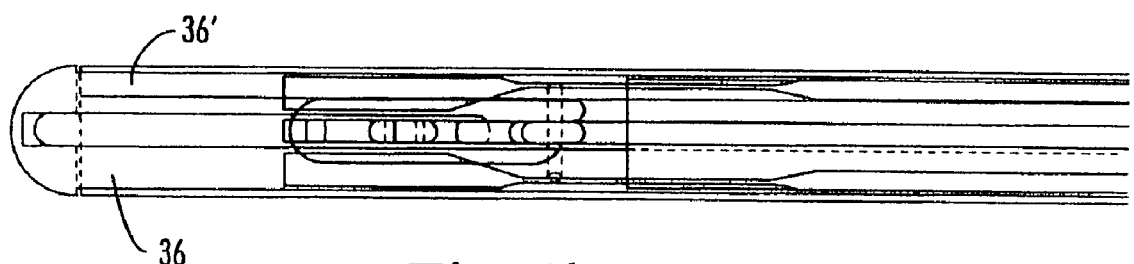
Figure 5C:
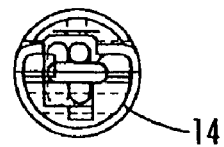

Referring now to FIGS. 4*a*, *b*, and *c*, the device 10 is shown in the at rest position. In the at rest position, a clip carrier/activator assembly 28 (shown generally within the area 28 shown in FIG. 4*a*) is retracted within the application sleeve 14. For purposes of this description, the preferred embodiment will be referred to as it is oriented in the drawings. Clearly, if the device 10 was pointed in the opposite direction, the references to right and left would be reversed. The invention will be described with the understanding that the distal end of the invention and of the applicator sleeve are to the left, and the proximal end of the invention and the elements of it are to the right. Thus, the clip carrier/activator assembly 28 is in its extreme most right position when the device 10 is at rest.

The applicator sleeve 14, in the preferred embodiment, has the shape of an elongated tube with a step down 30 formed in its distal end. While the applicator sleeve 14, in the preferred embodiment, is generally described as tubular and circular in cross section throughout the majority of its length, other cross-sectional shapes could be employed. The applicator sleeve has fingers 32 (FIG. 6*c*) curled over the step down portion 30 of its distal end. The pre-clamp arm 26 sits in the step down portion 30 of the applicator sleeve and fits within the envelope defined by the outer perimeter of the applicator sleeve 14 if that outer perimeter were extended beyond the left most tip of the device 10.

The pre-clamp arm 26 is elongated and, in the preferred embodiment, has an elongated slot 34 (FIG. 4*b*) defined by the two side arms 36, 36'. Depending nose 38 (FIG. 6*a*) is provided at the left end of the pre-clamp arm 26 and connector extension 40 (FIG. 4*b*) is formed with the pre-clamp arm 26 at its right end. Connector extension 40 has a hole 42 (FIG. 6*a*) through it and is formed with a camming surface 44 in the bottom right portion thereof.

A carrier arm 46 (FIG. 6*a*) extends from the applicator sleeve 14 beyond the step down portion 30 toward the distal end of the device. The carrier arm 46 may be U-shaped in cross section or any other convenient configuration. In the preferred embodiment, the carrier arm 46 is U-shaped and has a base 48 and upwardly projecting legs 50. A pin 52 extends through hole 42 and through holes in the legs 50 to connect the pre-clamp arm 26 to the carrier arm 46. The carrier arm 46 has a step up 54 along the base 48 and located beneath the camming surface 44. A spring 56 is connected to the carrier arm 46 and the bottom of the pre-clamp arm 26, directly to the left of the pivot point of connection pin 52. The spring 56 is biased such that it tends to pressure the pre-clamp arm 26 for clockwise movement (as viewed in FIG. 6*a*) about the pivot point 52.

Extending through the length of the applicator sleeve 14 along the upper side thereof is push rod 58. A ramp 60 is formed in the left end of push rod 58, and when the device is at rest, the push rod 58 is pushed to the left as can be seen in FIG. 4*a*. When push rod 58 is extended to its left most extreme position, the camming surface 44 rides over the ramp 60, forcing the pre-clamp arm 26 to rotate about the pivot point 52 in a counter clockwise direction into the closed position as shown in FIG. 4*a*. The pressure of the camming surface 44 riding over the ramp 60 and forcing the counter clockwise rotation of the pre-clamp arm 26 about the pivot point 52 overcomes the pressure of spring 56 to hold the pre-clamp arm in a "closed" position. In the "closed" position, the depending nose 38 extends down and over the extreme left end of the applicator sleeve 14. Pre-clamp arm 26 does not move length-wise relative to the length of the applicator sleeve 14, its only movement is to pivot about the pin 52 being urged by spring 56 in a clockwise rotation to an open position when a push rod 58 is retracted toward the proximal end of the device and being rotated counter clockwise about pin 52 to the closed position when the push rod 58 is advanced toward the distal end of the device 10 and the camming surface 44 is forced to ride over the ramp 60.

In operation, the purpose of the pre-clam arm 26 is to fit over a blood vessel or artery 62 (See FIG. 6*a*) and to flatten the vein so that it will be dimensionally sized to fit within the mouth of ligation clip 16 when pressure arm 22 is rotated in a clockwise direction to open the clip.

Figure 10A:
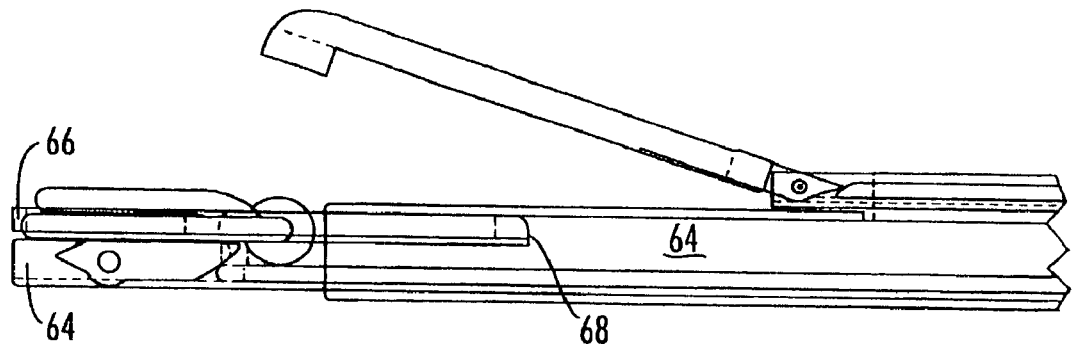
FIGS. 10a, 10b and 10c show side, top and end views of the device of the present invention with the clip assembly extending beyond the end of the sleeve and the wings of the device releasing the clip.
Figure 10B:
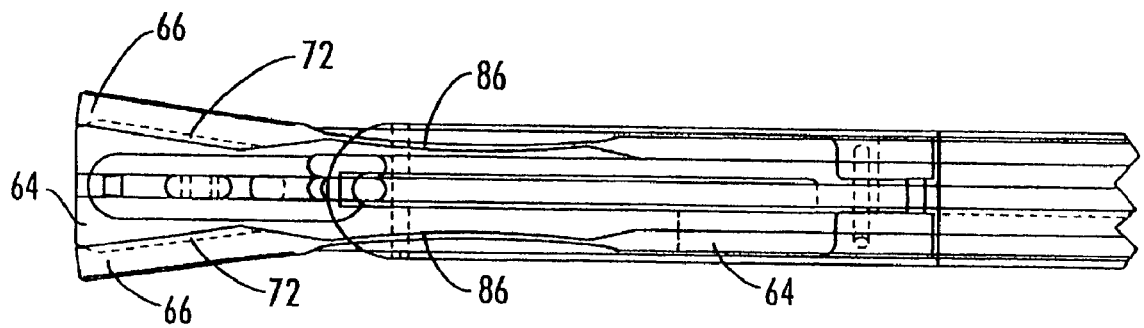
Figure 10C:
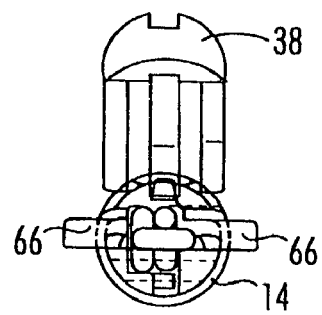

The ligation clip carrier/activator assembly 28 will now be described. In the at rest position, the ligation clip carrier/activator assembly 28 is retracted into the applicator sleeve 14 toward the proximal end of the device as is shown in FIG. 4*a*. In the at rest position, device 10 is inserted through a trocar for use in a surgical procedure. Once the device 10 is inserted through a trocar into a body cavity, the clip carrier/activator assembly 28 is advanced to the ready position shown in FIG. 5*a*. The assembly 28 is captured on the distal end of the device beneath the fingers 32. The assembly 28 includes clip carriage 64 and wings 66. The clip carriage 64 is an elongated element that fits within the applicator sleeve 14 and is telescopically moveable within the applicator sleeve 14. The clip carriage 64 also extends beneath the wings 66 as can be seen in FIGS. 10*a* and 10*b*.

Figure 11:
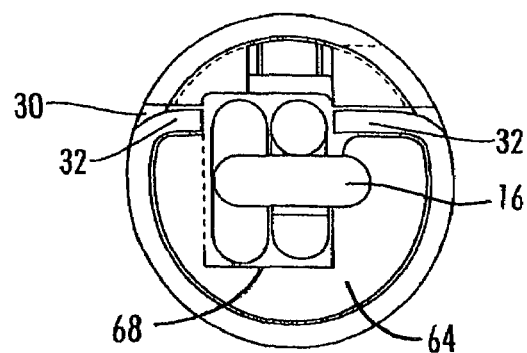
FIG. 11 shows a cross section of the device of the present invention along the length of the trunk.

The ligation clips 16 are stacked within the clip carriage 64 with the proximal end 24 of each clip aligned to the right as is seen in FIG. 2*a*. The trunk 68 (FIG. 10*a*) of the clip carriage 64 is that portion of the clip carriage to the right of the assembly 28 as shown in FIG. 4*a*. The cross section of the trunk 68 of the clip carriage 64 is shown in FIG. 11. As can be seen from FIG. 11, the cross section of the trunk 68 is shaped to mate with the cross section of the ligation clips 16 so that the ligation clips 16 will be held in stacked alignment through the length of the trunk 68. A plate and spring (not shown) are incorporated in the extreme right end of the trunk 68 of the clip carriage 64 to apply pressure against the proximal end 24 of the clip in the extreme right location of the device 10. The spring applies force against the plate to pressure the clips toward the distal end of the device. Thus, after each clip is applied to a vein, another clip is forced into a ready position for application to another vein.

Figure 12:
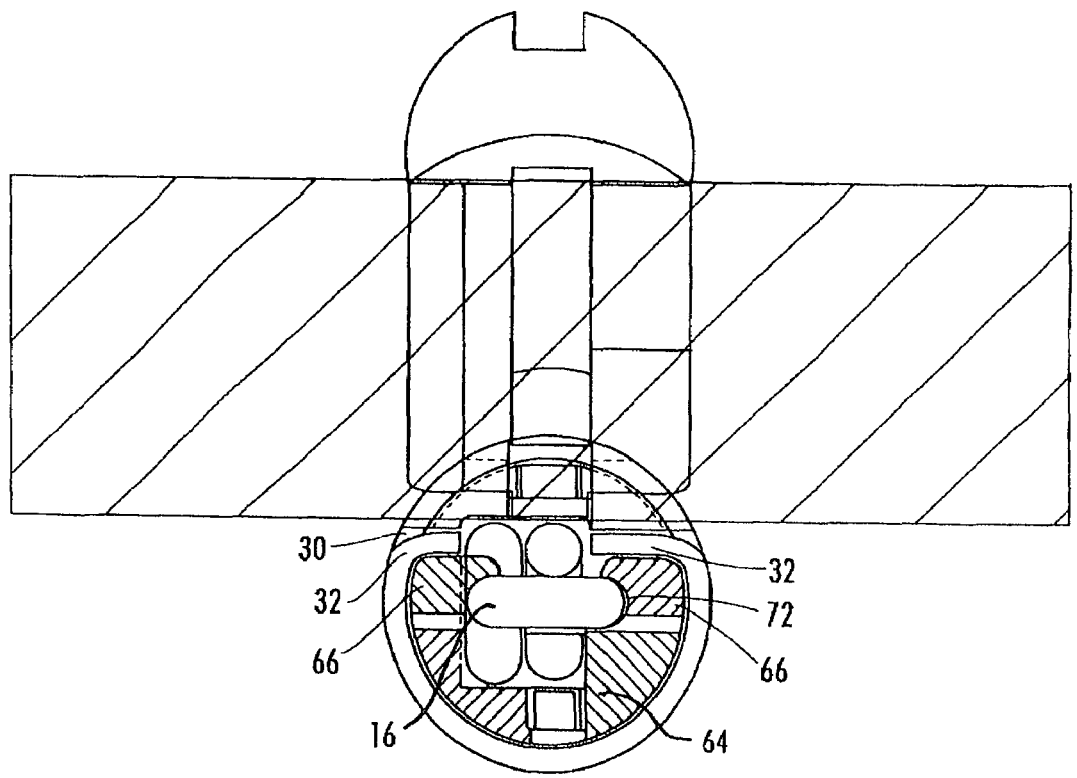
FIG. 12 shows a cross section of the device of the present invention taken to the left of the trunk.

In the region of the clip carrier/activator assembly 28 (see FIG. 4*a*), the clip carriage has a modified cross section. The general shape of the cross section of the clip carriage 64 in the region of the clip carrier/activator assembly 28 is shown in FIG. 12. As can be seen there, clip carriage 64 has a substantially semi-circular outer perimeter (the outer perimeter is of a shape to mate with the shape of the inner surface of the channel through the applicator sleeve 14), and the shape of the interior portion of the clip carriage 64 at this point is designed to mate with the lower portion of the cross sectional shape of the ligation clip 16. However, beneath the channel formed by the two legs of the U-shaped base 20 of the clip 16 is a channel to house the ligation clip opening assembly. At this cross-sectional point of the device, above the base portion of the clip carriage 64 are located the wings 66. Wings 66 have an elongated dimple 72 of a shape to mate with the upper and outer perimeter of the ligation clip 16. Because the wings 66 are held beneath the fingers 32, the elongated dimple 72 allows the wings to hold the clip in place against the pressure necessary to open the clip in the fashion that will be disclosed herein.

Figure 6A:
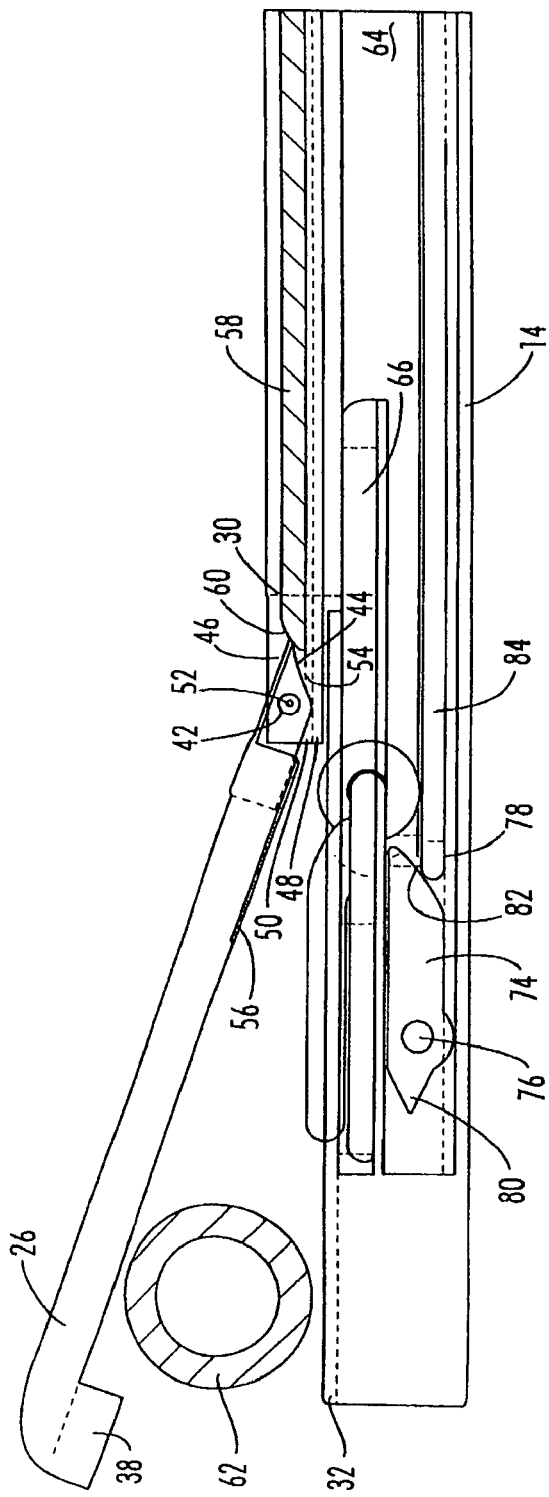
FIGS. 6a, 6b and 6c show side, top and end views respectively of the device of the present invention with the pre-clamp arm opened.
Figure 6B:
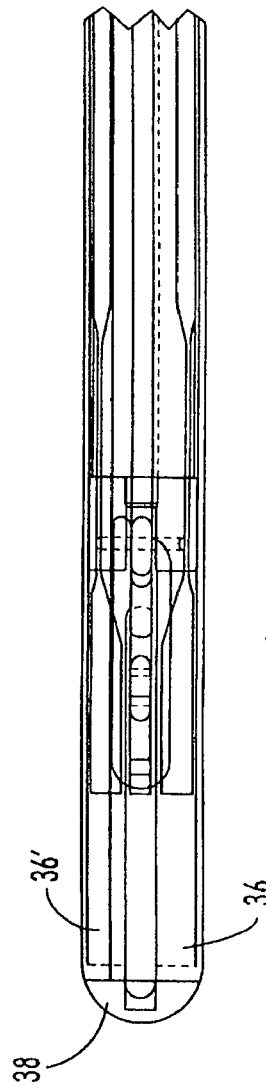
Figure 6C:
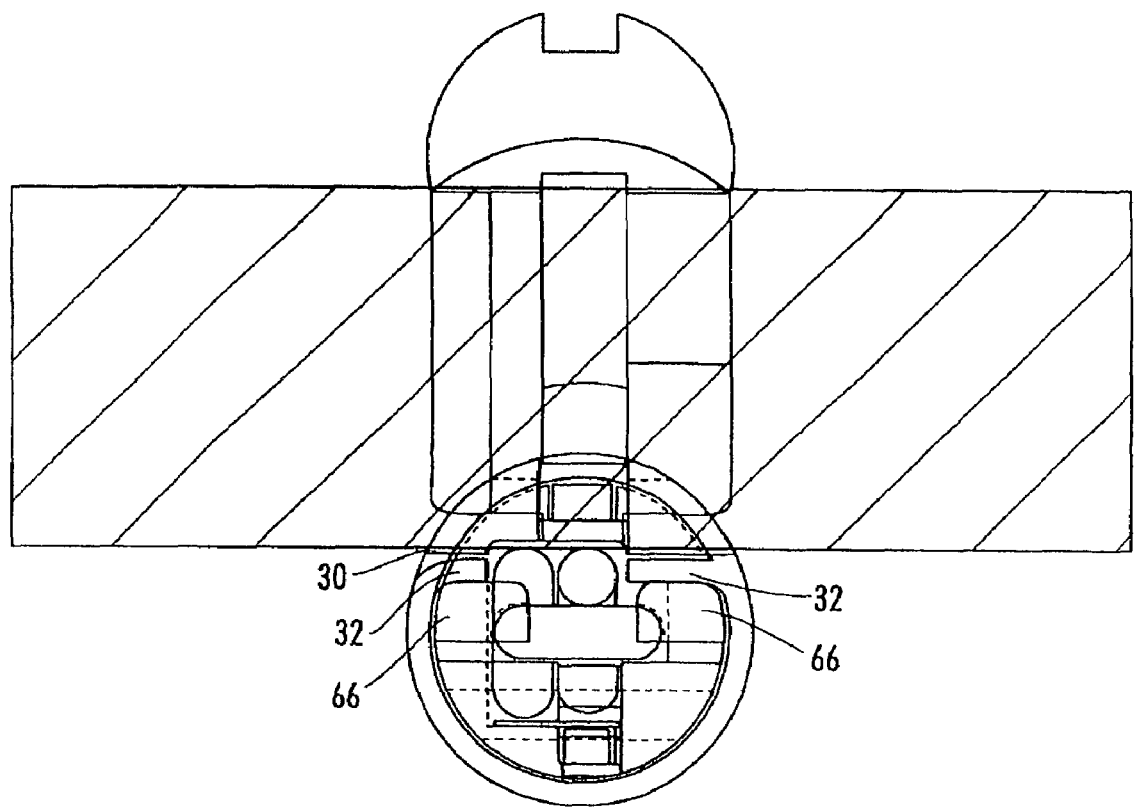
Figure 8A:
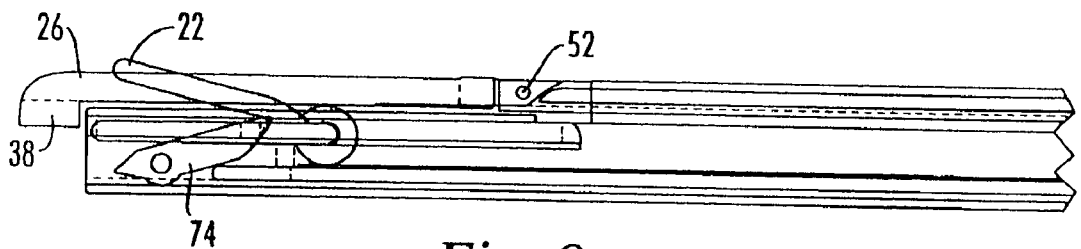
FIGS. 8a, 8b and 8c show the side, top and end views respectively of the device of the present invention with the pre-clamp arm closed and the ligation clip opened.
Figure 8B:
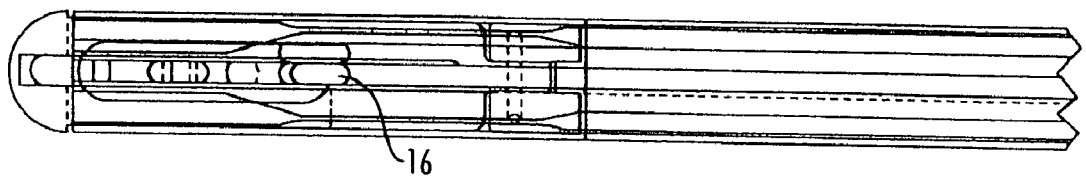
Figure 8C:
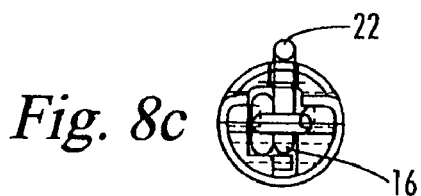
Figure 9C:
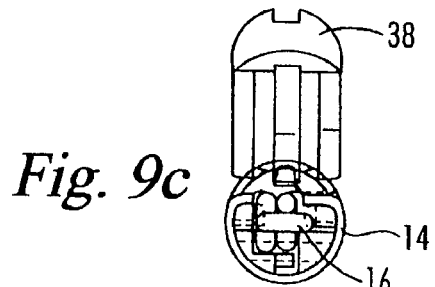
FIGS. 9a, 9b and 9c show the side, top and end views of the device of the present invention in the position as occurs immediately following the position as shown in FIG. 8.
Figure 9A:
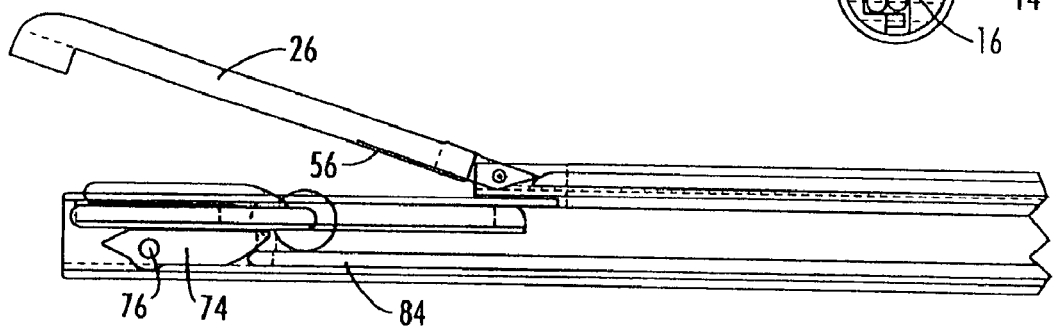
Figure 9B:

The ligation clip opening assembly housed in the bottom most portion of the clip carriage 64 includes a depressor 74 (FIG. 6a). The depressor 74 is generally pencil shaped, approximately the length of the channel between the two legs of the base 20 of the ligation clip 16 and of a cross sectional profile of a size that will allow at least a portion of the depressor 74 to extend through the channel between the two legs of the base 20 of the ligation clip 16. The depressor 74 is pivotally connected at 76 at its distal end to the upwardly projecting side walls of the clip carriage 64 and is permitted limited rotation about its pivotal connection 76. When the depressor 74 is in the at rest position, it lies flat along the base 78 of the clip carriage 64. A stop protrusion 80 is located on the depressor 74 to the left of the pivotal connection 76 to limit the rotation of the depressor 74. The depressor 74, from its at rest position, can only rotate in a counter clockwise direction (as viewed in FIG. 6a) and is limited in its movement because the stop protrusion 80 will engage the base 78 of the carriage assembly 64 after a limited counter clockwise rotation.

The depressor 74 has a cam surface 82 at its proximal end. The cam surface 82 is in contact with the distal end of the clip actuation push rod 84. The clip actuation push rod 84 is an elongated rod that fits within a channel in the base of the clip carriage 64 and is allowed to move to and fro within that channel from the at rest position shown in FIG. 6a to the trigger position shown in FIG. 7a and back to the at rest position of FIG. 6a. When the clip actuation push rod 84 is advanced to the left into the trigger position shown in FIG. 7a, the cam surface 82 of the depressor 74 rides up over the end of the clip actuation push rod 84 to rotate the depressor in a counter clockwise position. The proximal end of the depressor protrudes into the channel between the two legs of the base 20 of the ligation clip 16 against the under side of the pressure arm 22 of the clip and forces the clip into the open position shown in FIG. 2d and in FIG. 7a. As the ligation clip 16 is being opened by the action of the depressor 74 against the pressure arm 22 of the clip, the entire clip carriage assembly is advanced toward the distal end of the device 10 in relationship to the applicator sleeve 14 so that the clip will capture the vessel 62 that has been flattened by the action of the pre-clamp arm 26. The vessel will then be captured between the upper surface of the base 20 of the ligation clip 16 and the lower surface of the pressure arm 22 of the ligation clip 16 and the clip actuation push rod 84 can be retracted toward the proximal end of the device, allowing the depressor 74 to rotate back into the at rest position and release the pressure arm 22 to capture and close the vessel 62.

The next step in the procedure is to advance the clip carriage assembly 64 relative to the applicator sleeve 14 beyond the distal end of the applicator sleeve 14 (See FIGS. 10a and b). The wings 66 are connected to the clip carriage 64 by ribbon springs 86. The ribbon springs 86 are loaded to pressure the wings 66 to fan away from each other in the manner shown in FIG. 10b. The wings 66 will remain in parallel relationship so long as they are held within the applicator sleeve 14; however, once the wings 66 extend beyond the proximal end of the applicator sleeve 14, they are free to follow the pressure of the ribbon springs 86 and fan away from each other. The opening of the wings 66 releases the clip from the restraint of the elongated dimple 72 and thus the clip 16 is released from the device. The distal tip of the device can be tipped slightly to allow the ligation clip 16 to clear the device 10 as the clip 16 holds onto the vessel 62 in the clamped position. At this point, the clip carriage assembly is retracted toward the proximal end of the device relative to the applicator sleeve 14, the wings are returned within the confines of the applicator sleeve 14, another clip is released to advance to the ready position and the procedure can be performed again.

The mechanism for activating the pre-clamp arm and the clip assembly will now be described. Referring to FIG. 3, a cut away portion of the applicator sleeve shows the push rod 58 and the clip actuation push rod 84. The pistol grip 12 is shown with the cover removed so that the operation of the device can be described. The housing 88 of the pistol grip 12 can be constructed of any convenient sturdy material. Within the housing 88 of the pistol grip 12 is a pre-clamp push rod lever 90 which is hinged at 92 via a pin connected to housing 88. The pre-clamp push rod lever 90 has opposing ends, one end 94 pivotally connected to the proximal end of push rod 58 and the opposite end connected at pivot point 96 to the trigger 98. The trigger 98 fits within slots 100, 100' which allows the trigger 98 to traverse back and forth within the slots 100, 100' in response to pressure on the trigger by the user of the device 10. The return spring 102 is an expansion spring connected at one end against a stop 104 and at the other end against the inside of the trigger 98. Thus, a user of the device applies pressure to the trigger 98 to force the trigger 98 to move to the right within the slots 100, 100'. The trigger 98 will return to its at rest position (its position to the extreme left within the device shown in FIG. 3) when the pressure applied by the user is released. When the trigger 98 is activated by pressure from the user to move the trigger 98 to the right, the lever 90 rotates about the pin point 92. The end at connection point 96 of lever 90 will move toward the proximal end of the device 10 and the end at pivot point 94 will move in the direction of the distal end of the device 10, thus causing the push rod 58 to move toward the distal end of the device 10 and causing the ramp 60 to ride beneath the camming surface 44 and force the pre-clamp arm 26 into a closed position.

In the use of the device, the trigger 98 will be activated by the user to close the pre-clamp arm 26 while the device is being inserted through a trocar. Once a vein 62 that is to be ligated is located, the trigger 98 will be released, the pressure of spring 92 will force the trigger to move to the at rest position thereby rotating the lever 90 in a clockwise direction, retracting the push rod 58 toward the proximal end of the device and allowing the pre-clamp arm 26 to open. The device 10 will then be manipulated so that a vessel 62 is captured between the upper surface of the fingers 32 and the lower surface of the arm 26 and toward the proximal end of the depending nose 38 of the device. Once the vessel 62 is in position, the trigger 98 is activated by the user to cause a counter clockwise rotation of the lever 90 forcing the push rod 58 toward the distal end of the device and causing the pre-clamp arm to rotate counter clockwise about the pin 52 and compress the vessel 62 in the manner shown in FIG. 7a. While holding the trigger 98 in the activated position, thus holding the pre-clamp arm 26 against the vessel 62 in the manner shown in FIG. 7a, the user of the device next activates the clip carrier/activator assembly 28 through the use of the activator key 106.

Key 106 is contained within the housing 88 of the pistol grip 12 in slots similar to the slots 100, 100' which retain the trigger 98. Key 106 is allowed to move between an at rest position as is shown in FIG. 3 and an activated position which is to the right of the at rest position. Spring 108 is connected at one end to stop 110 and at the other end to the inside of the key 106. Spring 108 is an expansion spring which tends to force the key 106 to the at rest position shown in FIG. 3.

Clip carriage actuation lever 112 is pivotally connected to the housing 88 at pivot point 114. Lever 112 extends down from pivot point 114 to a pivot connection 116 between the depending leg of the lever 114 and the key 106. Thus, when the key 106 is activated, moving it in the direction of the proximal end of the device, the lever 112 is rotated in a counter clockwise direction about the pivot point 114. Moving the lever 112 in a counter clockwise direction about the point 114 causes the upper leg of the lever 112 to move generally toward the distal end of the device. The upper portion of the lever 112 is connected to the clip carriage 64 via the link 118. The link 118 is pivotally connected at one end 120 to the lever 112 and at the opposite end 122 to a boss 124 formed on the clip carriage 64. By the linkage just described, when the key 106 is activated, the clip carriage 64 moves toward the distal end of the device relative to the applicator sleeve 14 which at all times remains in a fixed position in relationship to the housing 88 of the pistol grip 12. By activating the key 106, through the operation of the clip actuation cam follower 126, the clip actuation push rod 84 is advanced relative to the clip carriage 64 concurrently with the movement of the clip carriage 64 relative to the sleeve 14. The clip actuation cam follower is pivotally connected at 128 to the upper portion of the lever 112 so that when the upper portion of the lever 112 moves in the direction of the distal end of the device, the cam follower 126 rides over the clip actuation cam 130 causing the clip actuation cam follower 126 to rotate in a clockwise direction relative to the lever 112. The clip actuation push rod 84 is connected at its proximal end to the depending leg of the clip actuation cam follower 126 at 132. Thus, the clip actuation push rod 84 moves toward the distal end of the device relative to the clip carriage assembly 64 and causes the depressor 74 to ride over the distal end of the clip activation push rod, forcing the depressor upwardly against the pressure arm 22 of the ligation clip 16.

By the mechanism described, the activation of key 106 advances the clip carriage assembly to the position shown in FIG. 7a. Continued pressure on the key 106 advances the clip actuation cam follower 126 over the clip actuation cam 130 so that the follower 126 disengages from the cam 130. A coil spring (not shown) is provided at the pivot point 128 tending to force the cam follower 126 to rotate in a counter clockwise direction. Thus, as soon as the cam follower 126 releases from the cam 130 after it passes over the cam 130, the spring about the pivot point 128 will force the cam follower 126 to rotate in a counter clockwise direction thereby causing the clip actuation push rod 84 to retract toward the proximal end of the device. When the clip actuation push rod 84 retracts toward the proximal end of the device, the pressure of the depressor 74 is relieved from the underside of the pressure arm 22 and the pressure arm 22 closes on the vessel 64, capturing the vessel 64 between the underside of the pressure arm 22 and the top side of the base 20 of the clip 16.

To release the clip 16 from the device, additional pressure is applied to the key 106 thus forcing the clip assembly 64 to advance further in the direction of the distal end of the device relative to the stationary sleeve 14, forcing the wings 66 beyond the distal end of the sleeve 14 so that wings 66 may fan open and release the clip 16.

In order to return the device to the at rest or ready position for insertion of another clip, pressure on the key 106 is released. Spring 108 forces the key 106 toward the proximal end of the device thus rotating the lever 112 about the point 114 in a clockwise direction. The entire device is then reset. The cam follower 126 is allowed to pass back to the ready position by virtue of the pivotal connection of the cam 130 to the housing 88. The cam 130 is pivotally connected at 134 to the housing 88 and the cam 130 has a ramp 136 formed on the surface of the cam 130 that faces the housing 88 of the grip 12 shown in FIG. 3. The cam 130 has a spring (not shown) tending to force the cam 130 against the housing 88 as shown in FIG. 3. When the cam follower 126 is returned to the at rest position, it will ride against the ramp 136 causing the cam 130 to rotate about the pivot point 134 and slip up slightly to allow the cam follower 126 to pass between the cam 130 and the housing 88. Once the cam follower 126 clears the cam 130, the spring will rotate the cam 130 back to the ready position as is shown in FIG. 3.

Relieving the pressure on the key 106 also causes the clip cartridge 64 to retract toward the proximal end of the device into the ready position.

A locking lever 137 is also provided on the lever 112 and pivotally connected to the lever 112 at point 138. The locking lever 137 fits over the lever 90 so that when the key 106 is in the at rest position and the lever 112 is rotated into its clockwise most position, the locking lever 137 will hold the lever 90 in the position that would occur if the trigger 98 were depressed. Thus, the push rod 58 is advanced forward to cause the pre-clamp arm 26 to be closed. This locking lever allows the device to be inserted through a trocar without the user having to hold the trigger 98 in an activated position. In operation, once pressure is applied to the key 106, the pressure of the locking lever 137 on the lever 90 is released allowing the spring 102 to push the trigger 98 toward the distal end of the device thereby retracting the push rod 58 and allowing the pre-clamp arm 26 of the device to open. Once the pre-clamp arm of the device is open, the pre-clamping pressure on a vessel 62 is created by activation of the trigger 98, thus forcing the push rod 58 toward the distal end of the device and causing the pre-clamp arm to close against the fingers 32.

Figure 13A:
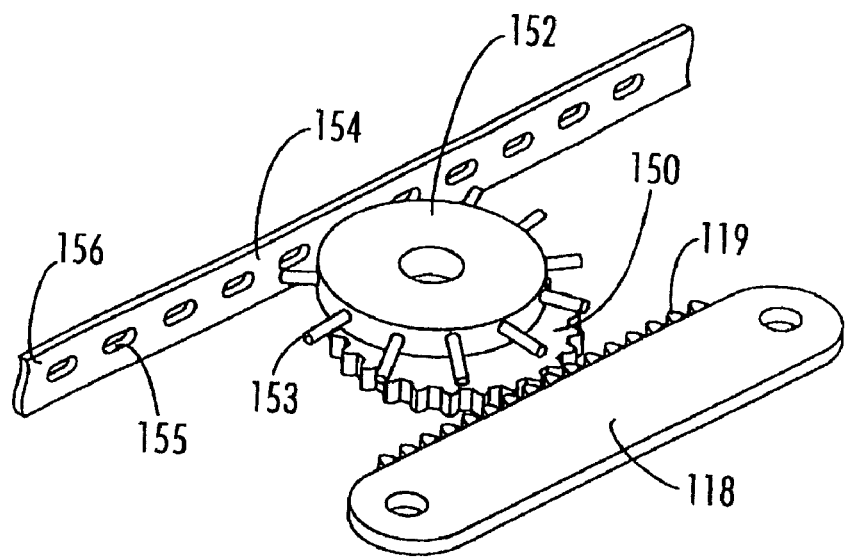
FIGS. 13a and 13b show a mechanism that can be incorporated in the device of the present invention to control advance of the clips into the ready position in the clip carriage.
Figure 13B:
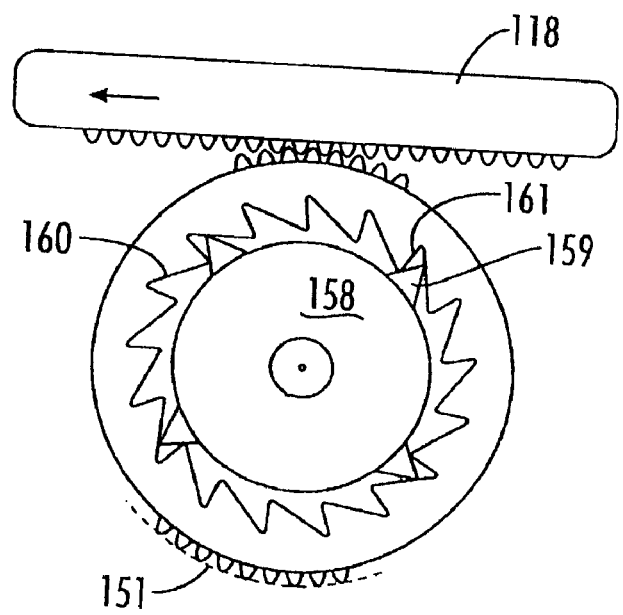

Once a clip has been applied in the manner described, a second clip is loaded into the ready position from the clip carriage 64 by the mechanism illustrated in FIGS. 13a and 13b forcing the ligation clip 16 to advance toward the distal end of the device.

The mechanism shown in FIGS. 13a and 13b is mounted in the pistol grip 12 directly adjacent link 118. The mechanism shown in FIGS. 13a and 13b is not illustrated in FIG. 3 for purpose of clarity. However, the additional mechanical structures shown in FIGS. 13a and 13b are mounted directly above link 118 and in engagement therewith.

Referring now specifically to FIGS. 13a and 13b, there is illustrated a clip pushrod 154 which is slidably mounted within the pistol grip 12 and permitted to move in a lineal direction along its length. The distal end 156 of the clip pushrod 154 will be in engagement with the rear most ligation clip 16 in the magazine of clips positioned in the carriage passageway. Movement of the clip pushrod 154 toward the distal end of the device will force the forward most ligation clip 16 into the carriage assembly.

The controlling mechanism for advancing the ligation clips is provided by link 118 which has teeth 119 on the upper edge thereof in mating engagement with teeth 151 on the outer perimeter of the one-way ratchet clutch 150. The cog wheel 152 is mounted to rotate with the one-way ratchet clutch 150 and is coaxially aligned with the one-way ratchet clutch 150. The cogs 153 on the cog wheel 152 engage the cog ports 155 in the clip pushrod 154. In operation, as can be seen from FIG.

13b, upon forward motion of link 118 as is shown by the arrow in FIG. 13b, the one-way ratchet clutch 150 will rotate counter clockwise, but cog wheel hub 158 will not rotate because the teeth 159 protruding from the cog wheel hub 158 will ratchet over the ramped ratchet teeth 160. However, when the link 118 moves in the reverse direction, the engagement between the teeth 119 on the link 118 and the teeth 151 will cause the one-way ratchet clutch 150 to rotate in a clockwise direction, causing the tooth face 161 to engage the teeth 159 and rotate the hub 158 in a clockwise direction. FIG. 13b is viewed from the bottom of the assembly shown in FIG. 13a; thus, when viewed from the top, the only rotational movement of the cog wheel 152 will be in a counter clockwise direction upon the movement of the link 118 toward the proximal end of the device. When the link 118 moves toward the distal end of the device, the ratcheting mechanism will cause the cog wheel 152 to remain stationary.

The operation of the assembly shown in FIGS. 13a and 13b will thereby control the movement of a clip 16 from the ready position into the carriage assembly as follows: when the device is being reset, link 118 moves to the rear, causing cog wheel 152 to rotate, advancing clip pushrod 154 to load a new clip into the clip carriage. When the mechanism is activated and the link 118 moves forward, the cog wheel 152 remains stationary so that the clips 16 in the clip magazine do not advance. Thus, the mechanism as described retains the clips in the ready position until the mechanism is activated by the retracting carriage assembly 64 rotating the cog wheel 152 and advance the clip pushrod 154 so that a single clip moves forward and is permitted to advance into the carriage assembly.

As can be seen from FIG. 3, the device of the present invention can be used in a number of different procedures and the applicator sleeve 14 and related assemblies can be removed from the pistol grip and replaced with a clean sterile sleeve 14 for a second operative procedure with a new patient. The device is provided with a hinged cover 140 which is hinged to the housing 88 at 142. The closure mechanism 140 can be held in place by any convenient safety latch 144 (see FIG. 1). The housing is provided with upper and lower recesses 146 and 148 and the sleeve 14 can be provided with bosses (not shown) that fit within the upper and lower recesses 146, 148 to stabilize the position of the applicator sleeve 14 in relationship to the pistol grip 12. The pivotal connections 94, 122 and 132 can be designed so that the pins will slidably engage within the openings to permit the applicator sleeve 14 and related parts to be lifted from the pistol grip 12 and replaced by an applicator sleeve loaded with fresh ligation clips 16. To make this replacement, it is necessary that the face of the pistol grip 12 be removable from the pistol grip and have means for connecting the face onto the pistol grip 12 in a fixed relationship. Any convenient latching mechanism can be provided to connect the face of the pistol grip onto the body of the pistol grip 12.

Thus, although there have been described particular embodiments of the present invention of a new and useful "Low Profile Tool for Applying Spring Action Ligation Clips", it is not intended that such references be construed as limitations upon the scope of this invention except as set forth in the following claims. Further, although there have been described certain dimensions used in the preferred embodiment, it is not intended that such dimensions be construed as limitations upon the scope of this invention except as set forth in the following claims.

We claim:

1. A combination of a surgical ligation clip for ligating a vessel and a ligation clip applier for applying the ligation clip to the vessel, the combination comprising:

said ligation clip comprising a continuous length of material, said material having an elongated member having a proximal end, an opposite distal end, and a length therebetween, said material having an elongated arm having a proximal end, an opposite distal end, and a length therebetween, said arm having a vessel contacting surface oriented toward said member, said member having a surface oriented toward said vessel contacting surface of said arm, said arm and said member being biased toward one another in an open position, said material having a connector having a maximum length, and a maximum height perpendicular to the maximum length of said connector, said connector connecting said member and said arm, said clip having a longitudinal axis, a proximal end, an opposite distal end, and a length therebetween, said clip having a width proximate said distal end of said clip that is greater than a width proximate said proximal end of said clip, said surface of said member along at least a portion of the length of said member having a width corresponding to the width proximate said distal end of said clip, wherein one of said arm and said member includes a portion at said distal end thereof generally oriented along the longitudinal axis of said clip, and the maximum length of said connector is oriented along the longitudinal axis of said clip, the maximum length of said connector approximating the maximum height of said connector; and said clip applier comprising a proximal end, an opposite distal end, a length therebetween, and an opener pivotably attached to said clip applier proximate said distal end, said opener being actuatable from a first position to a second position, and said opener being adapted to contact said arm to move said clip to the open position upon actuation thereof toward the second position.

2. The clip of the combination of claim 1, wherein said surface of at least one of said arm and said member is treated to enhance gripping of the vessel.

3. The clip of the combination of claim 2, wherein said surface includes at least one of ridges, notches, burrs, and etching.

4. The clip of the combination of claim 1, wherein said connector includes a coil biasing said arm and said member toward one another in the open position.

5. The clip of the combination of claim 1, wherein said continuous length of material of at least one of said member and arm has a non-circular cross section along at least a portion of its length.

6. A combination of a surgical ligation clip for ligating a fluid carrying structure and a ligation clip applier for applying the ligation clip to the fluid carrying structure, the combination comprising:

said ligation clip comprising:

a longitudinal axis, a distal end, and a proximal end opposite said distal end;

a clamping arm oriented generally along the longitudinal axis of said clip, said clamping arm including a portion at said distal end of said clip generally oriented along the longitudinal axis;

a support member oriented generally along the longitudinal axis of said clip, said support member including a portion at said distal end of said clip generally oriented along the longitudinal axis; and a connector at said proximal end of said clip having a maximum length oriented along the longitudinal axis, and a maximum height perpendicular to the maximum length of said connector, the maximum length of said connector approximating the maximum height of said connector, said connector joining said support member and said clamping arm, said clip being formed of a continuous length of material having a first free end terminating at said connector and a second free end terminating proximate said distal end of said clip; and said clip applier comprising a proximal end, an opposite distal end, a length therebetween, and an opener pivotably attached to said clip applier proximate said distal end, said opener being actuatable from a first position to a second position, and said opener being adapted to contact said clamping arm to move said clip to an open position upon actuation thereof toward the second position.

7. The clip of the combination of claim 6, wherein said connector is adapted to bias said support member and said clamping arm toward one another in a closed position.

8. The clip of the combination of claim 6, wherein said connector includes a coil.

9. The clip of the combination of claim 6, wherein a surface of at least one of said clamping arm and said support member is treated to enhance gripping of the fluid carrying structure.

10. The clip of the combination of claim 9, wherein said surface includes at least one of ridges, notches, burrs, and etching.

11. The clip of the combination of claim 6, wherein said continuous length of material of at least one of said support member and clamping arm has a non-circular cross section along at least a portion of its length.

12. The clip of the combination of claim 1, wherein the other of said arm and said member includes a portion at said distal end thereof generally oriented along the longitudinal axis.

13. The clip of the combination of claim 1, wherein the length of said connector is less than half of the lengths of said arm and said member.

14. The clip of the combination of claim 1, wherein said connector biases said distal end of said arm away from said distal end of said member while said clip is in a closed and unengaged position.

15. A combination of a surgical ligation clip for ligating a fluid carrying structure and a ligation clip applier for applying the ligation clip to the fluid carrying structure, the combination comprising:

said ligation clip comprising:
a longitudinal axis, a distal end, and a proximal end opposite said distal end;
a support member having a maximum length oriented generally along the longitudinal axis of said clip;
a clamping arm having a maximum length oriented generally along the longitudinal axis of said clip, said clamping arm being biased toward said support member; and
a connector having a maximum length oriented along the longitudinal axis, and a maximum height perpendicular to the maximum length of said connector, the maximum length of said connector approximating the maximum height of said connector, and being less than half of the maximum lengths of one of said support member and said clamping arm, said clip being formed of a continuous length of material having a first free end terminating proximate said proximal end of said clip and a second free end terminating proximate said distal end of said clip; and said clip applier comprising a proximal end, an opposite distal end, a length therebetween, and an opener pivotably attached to said clip applier proximate said distal end, said opener being actuatable from a first position to a second position, and said opener being adapted to contact said clamping arm to move said clip to an open position upon actuation thereof toward the second position.

16. The clip of the combination of claim 15, wherein said clip includes a first bend section between said support member and said clamping arm.

17. The clip of the combination of claim 16, wherein said support member includes a second bend section.

18. A combination of a surgical ligation clip for ligating a fluid carrying structure and a ligation clip applier for applying the ligation clip to the fluid carrying structure, the combination comprising:

said ligation clip comprising:
a longitudinal axis, a distal end, and a proximal end opposite said distal end;
a clamping arm having a proximal end, a distal end opposite said proximal end, and a length therebetween, a portion of the length of said clamping arm at said distal end being generally parallel to the longitudinal axis;
a support member having a proximal end, a distal end opposite said proximal end, and a length therebetween, a portion of the length of said support member at said distal end being generally parallel to the longitudinal axis; and
a connector at said proximal end of said clip for connecting said clamping arm and said support member, said connector having a maximum length oriented along the longitudinal axis, and a maximum height perpendicular to the maximum length of said connector, the maximum length of said connector approximating the maximum height of said connector, and being less than half of the lengths of one of said clamping arm and said support member, said connector spacing said clamping arm and said support member apart from one another along a majority of the lengths thereof, and allowing for movement of said clamping arm and said support member relative to one another; and said ligation clip applier comprising a proximal end, an opposite distal end, a length therebetween, and an opener pivotably attached to said clip applier proximate said distal end, said opener being actuatable from a first position to a second position, and said opener being adapted to contact said clamping arm to move said clip to an open position upon actuation thereof toward the second position.

19. A combination of a surgical ligation clip for ligating a fluid carrying structure and a ligation clip applier for applying the ligation clip to the fluid carrying structure, the combination comprising:

said ligation clip comprising:
a longitudinal axis, a distal end, and a proximal end opposite said distal end;
a clamping arm having a proximal end, a distal end opposite said proximal end, and a length therebetween, a portion of the length of said clamping arm at said distal end being generally parallel to the longitudinal axis;
a support member having a proximal end, a distal end opposite said proximal end, and a length therebetween, a portion of the length of said support member at said distal end being generally parallel to the longitudinal axis; and a connector at said proximal end of said clip for connecting said clamping arm and said support member, said connector having a maximum length oriented along the longitudinal axis, and a maximum height perpendicular to the maximum length of said connector, the maximum length of said connector approximating the maximum height of said connector, said clamping arm and said support member spaced apart from one another along a majority of the lengths thereof, said connector allowing for movement of said clamping arm and said support member relative to one another; and said ligation clip applier comprising a proximal end, an opposite distal end, a length therebetween, and an opener pivotably attached to said clip applier proximate said distal end, said opener being actuatable from a first position to a second position, and said opener being adapted to contact said clamping arm to move said clip to an open position upon actuation thereof toward the second position.

* * * * *